US012753231B2

(12) United States Patent
Zhou et al.

(10) Patent No.: US 12,753,231 B2
(45) Date of Patent: Oct. 6, 2026

(54) NKG2A-TARGETING ANTIBODY AND USE THEREOF

(71) Applicant: BIOHENG THERAPEUTICS LIMITED, Grand Cayman (KY)

(72) Inventors: Yali Zhou, Nanjing (CN); Gong Chen, Nanjing (CN); Xiaoyan Jiang, Nanjing (CN); Tingting Guo, Nanjing (CN); Jiangtao Ren, Nanjing (CN); Xiaohong He, Nanjing (CN); Yanbin Wang, Nanjing (CN); Lu Han, Nanjing (CN)

(73) Assignee: BIOHENG THERAPEUTICS LIMITED, Grand Cayman (KY)

( * ) Notice: Subject to any disclaimer, the term of this patent is extended or adjusted under 35 U.S.C. 154(b) by 544 days.

(21) Appl. No.: 18/254,037

(22) PCT Filed: Nov. 18, 2021

(86) PCT No.: PCT/CN2021/131435
§ 371 (c)(1),
(2) Date: May 23, 2023

(87) PCT Pub. No.: WO2022/105826
PCT Pub. Date: May 27, 2022

(65) Prior Publication Data

US 2024/0043532 A1 Feb. 8, 2024

(30) Foreign Application Priority Data

Nov. 23, 2020 (CN) ......................... 202011320557.5

(51) Int. Cl.

| | |
|---|---|
| ***A61K 39/00*** | (2006.01) |
| ***C07K 16/28*** | (2006.01) |
| ***C12N 5/0783*** | (2010.01) |
| ***C12N 15/63*** | (2006.01) |

(52) U.S. Cl.
CPC .......... *C07K 16/2803* (2013.01); *A61K 39/00* (2013.01); *A61K 39/001111* (2018.08); *C12N 5/0636* (2013.01); *C12N 15/63* (2013.01); *A61K 2039/5156* (2013.01); *C07K 2317/31* (2013.01); *C07K 2317/565* (2013.01)

(58) Field of Classification Search
None
See application file for complete search history.

(56) References Cited

U.S. PATENT DOCUMENTS

| | | | | |
|---|---|---|---|---|
| 8,796,427 B2 * | 8/2014 | Spee | ........................ | A61P 29/00 530/388.22 |
| 2019/0135938 A1 * | 5/2019 | Moretta | .................... | A61P 3/10 |

FOREIGN PATENT DOCUMENTS

| | | | |
|---|---|---|---|
| CN | 101952317 | A | 1/2011 |
| CN | 111153995 | A | 5/2020 |
| JP | 2011510047 | A | 3/2011 |
| JP | 2020510101 | A | 4/2020 |
| WO | 2009092805 | A1 | 7/2009 |
| WO | 2012172102 | A1 | 12/2012 |
| WO | 2020094071 | A1 | 5/2020 |
| WO | 2022257937 | A1 | 12/2022 |

OTHER PUBLICATIONS

Ferrara et al, 2015.*
Lerner Nature 1982; 299:592-596.*
Lloyd et al., 2009, Protein Engineering, v.22, pp. 159-168.*
First office action of counterpart Australian patent application No. 2021383237, dated Mar. 17, 2025.
First office action of counterpart Canadian patent application No. 3, 199,640, dated Jul. 23, 2024.
First office action of counterpart Japanese patent application No. 2023-530941, dated May 7, 2021.
First office action of counterpart Korean patent application No. 10-2023-7018136, dated Nov. 19, 2025.
Supplementary European Search Report of counterpart application EP 218939734 dated Mar. 24, 2024.
Thorbald van Hall et al., Monalizumab: inhibiting the novel immune checkpoint NKG2A, Journal for Immuno Therapy of Cancer, (2019) 7:263.
English Abstract of cited patent documents.
English translation of ISR of WO2022105826.
International Search Report of WO2022105826.
Written Opinion of The International Searching Authority of WO2022105826.

* cited by examiner

*Primary Examiner* — Michail A Belyavskyi
(74) *Attorney, Agent, or Firm* — Platinum Intellectual Property PC

(57) ABSTRACT

Provided are an NKG2A-targeting antibody, and a multi-specific antibody, a chimeric receptor, an antibody conjugate, a pharmaceutical composition and a kit which comprise same, and the use thereof in the diagnosis/treatment/prevention of diseases associated with NKG2A expression.

5 Claims, 2 Drawing Sheets

Specification includes a Sequence Listing.

SEQUENCE LISTING

```
<160> NUMBER OF SEQ ID NOS: 38

<210> SEQ ID NO 1
<211> LENGTH: 11
<212> TYPE: PRT
<213> ORGANISM: Artificial Sequence
<220> FEATURE:
<223> OTHER INFORMATION: CDR-L1

<400> SEQUENCE: 1

Ser Ala Ser Ser Ser Val Ser Ser Tyr Ile Tyr
1               5                   10


<210> SEQ ID NO 2
<211> LENGTH: 7
<212> TYPE: PRT
<213> ORGANISM: Artificial Sequence
<220> FEATURE:
<223> OTHER INFORMATION: CDR-L2

<400> SEQUENCE: 2

Leu Thr Ser Asn Leu Ala Ser
1               5


<210> SEQ ID NO 3
<211> LENGTH: 9
<212> TYPE: PRT
<213> ORGANISM: Artificial Sequence
<220> FEATURE:
<223> OTHER INFORMATION: CDR-L3

<400> SEQUENCE: 3
```

Gln Gln Trp Ser Gly Asn Pro Tyr Thr
1               5

<210> SEQ ID NO 4
<211> LENGTH: 7
<212> TYPE: PRT
<213> ORGANISM: Artificial Sequence
<220> FEATURE:
<223> OTHER INFORMATION: CDR-H1

<400> SEQUENCE: 4

Gly Phe Thr Phe Ser Ser Tyr
1               5

<210> SEQ ID NO 5
<211> LENGTH: 6
<212> TYPE: PRT
<213> ORGANISM: Artificial Sequence
<220> FEATURE:
<223> OTHER INFORMATION: CDR-H2

<400> SEQUENCE: 5

Ser Ser Gly Gly Ser Tyr
1               5

<210> SEQ ID NO 6
<211> LENGTH: 10
<212> TYPE: PRT
<213> ORGANISM: Artificial Sequence
<220> FEATURE:
<223> OTHER INFORMATION: CDR-H3

<400> SEQUENCE: 6

His Gly Asp Tyr Pro Arg Phe Phe Asp Val
1               5                   10

<210> SEQ ID NO 7
<211> LENGTH: 107
<212> TYPE: PRT
<213> ORGANISM: Artificial Sequence
<220> FEATURE:
<223> OTHER INFORMATION: hZ199 VL

<400> SEQUENCE: 7

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Ser Tyr
            20                  25                  30

Ile Tyr Trp Tyr Gln Gln Lys Pro Gly Gln Ala Pro Arg Leu Leu Ile
        35                  40                  45

Tyr Leu Thr Ser Asn Leu Ala Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Trp Ser Gly Asn Pro Tyr
                85                  90                  95

Thr Phe Gly Gln Gly Thr Lys Leu Glu Ile Lys
            100                 105

<210> SEQ ID NO 8
<211> LENGTH: 119
<212> TYPE: PRT
<213> ORGANISM: Artificial Sequence
<220> FEATURE:
<223> OTHER INFORMATION: hZ199 VH

<400> SEQUENCE: 8

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Ala Lys Ser Trp Val Arg Gln Ala Pro Gly Lys Gly Leu Glu Trp Val
35 40 45

Ser Glu Ile Ser Ser Gly Gly Ser Tyr Thr Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg His Gly Asp Tyr Pro Arg Phe Phe Asp Val Trp Gly Gln Gly
100 105 110

Thr Thr Val Thr Val Ser Ser
115

<210> SEQ ID NO 9
<211> LENGTH: 244
<212> TYPE: PRT
<213> ORGANISM: Artificial Sequence
<220> FEATURE:
<223> OTHER INFORMATION: hZ199 scFv

<400> SEQUENCE: 9

Glu Ile Val Leu Thr Gln Ser Pro Ala Thr Leu Ser Leu Ser Pro Gly
1 5 10 15

Glu Arg Ala Thr Leu Ser Cys Ser Ala Ser Ser Ser Val Ser Ser Tyr
20 25 30

Ile Tyr Trp Tyr Gln Gln Lys Pro Gly Gln Ala Pro Arg Leu Leu Ile
35 40 45

Tyr Leu Thr Ser Asn Leu Ala Ser Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Trp Ser Gly Asn Pro Tyr
85 90 95

Thr Phe Gly Gln Gly Thr Lys Leu Glu Ile Lys Gly Ser Thr Ser Gly
100 105 110

Ser Gly Lys Pro Gly Ser Gly Glu Gly Ser Thr Lys Gly Glu Val Gln
115 120 125

Leu Val Glu Ser Gly Gly Gly Leu Val Lys Pro Gly Gly Ser Leu Arg
130 135 140

Leu Ser Cys Ala Ala Ser Gly Phe Thr Phe Ser Ser Tyr Ala Lys Ser
145 150 155 160

Trp Val Arg Gln Ala Pro Gly Lys Gly Leu Glu Trp Val Ser Glu Ile
165 170 175

Ser Ser Gly Gly Ser Tyr Thr Tyr Tyr Ala Asp Ser Val Lys Gly Arg
180 185 190

Phe Thr Ile Ser Arg Asp Asn Ala Lys Asn Ser Leu Tyr Leu Gln Met
195 200 205

Asn Ser Leu Arg Ala Glu Asp Thr Ala Val Tyr Tyr Cys Ala Arg His

```
    210                 215                 220

Gly Asp Tyr Pro Arg Phe Phe Asp Val Trp Gly Gln Gly Thr Thr Val
225                 230                 235                 240

Thr Val Ser Ser


<210> SEQ ID NO 10
<211> LENGTH: 107
<212> TYPE: PRT
<213> ORGANISM: Artificial Sequence
<220> FEATURE:
<223> OTHER INFORMATION: hZ199-V1 VL

<400> SEQUENCE: 10

Glu Ile Val Leu Thr Gln Ser Pro Ala Thr Leu Ser Leu Ser Pro Gly
1               5                   10                  15

Glu Arg Ala Thr Met Ser Cys Ser Ala Ser Ser Ser Val Ser Ser Tyr
            20                  25                  30

Ile Tyr Trp Tyr Gln Gln Lys Pro Gly Gln Ala Pro Arg Leu Leu Ile
        35                  40                  45

Tyr Leu Thr Ser Asn Leu Ala Ser Gly Val Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Thr Tyr Tyr Cys Gln Gln Trp Ser Gly Asn Pro Tyr
                85                  90                  95

Thr Phe Gly Gln Gly Thr Lys Leu Glu Ile Lys
            100                 105


<210> SEQ ID NO 11
<211> LENGTH: 119
<212> TYPE: PRT
<213> ORGANISM: Artificial Sequence
<220> FEATURE:
<223> OTHER INFORMATION: hZ199-V1 VH

<400> SEQUENCE: 11

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Glu Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg His Gly Asp Tyr Pro Arg Phe Phe Asp Val Trp Gly Gln Gly
            100                 105                 110

Thr Leu Val Thr Val Ser Ser
        115


<210> SEQ ID NO 12
<211> LENGTH: 244
<212> TYPE: PRT
<213> ORGANISM: Artificial Sequence
<220> FEATURE:
<223> OTHER INFORMATION: hZ199-V1 scFv
```

<400> SEQUENCE: 12

Glu Ile Val Leu Thr Gln Ser Pro Ala Thr Leu Ser Leu Ser Pro Gly
1 5 10 15

Glu Arg Ala Thr Met Ser Cys Ser Ala Ser Ser Ser Val Ser Ser Tyr
20 25 30

Ile Tyr Trp Tyr Gln Gln Lys Pro Gly Gln Ala Pro Arg Leu Leu Ile
35 40 45

Tyr Leu Thr Ser Asn Leu Ala Ser Gly Val Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Thr Tyr Tyr Cys Gln Gln Trp Ser Gly Asn Pro Tyr
85 90 95

Thr Phe Gly Gln Gly Thr Lys Leu Glu Ile Lys Gly Ser Thr Ser Gly
100 105 110

Ser Gly Lys Pro Gly Ser Gly Glu Gly Ser Thr Lys Gly Glu Val Gln
115 120 125

Leu Val Glu Ser Gly Gly Gly Leu Val Lys Pro Gly Gly Ser Leu Arg
130 135 140

Leu Ser Cys Ala Ala Ser Gly Phe Thr Phe Ser Ser Tyr Ala Met Ser
145 150 155 160

Trp Val Arg Gln Ala Pro Gly Lys Gly Leu Glu Trp Val Ala Glu Ile
165 170 175

Ser Ser Gly Gly Ser Tyr Thr Tyr Tyr Pro Asp Ser Val Lys Gly Arg
180 185 190

Phe Thr Ile Ser Arg Asp Asn Ala Lys Asn Ser Leu Tyr Leu Gln Met
195 200 205

Asn Ser Leu Arg Ala Glu Asp Thr Ala Val Tyr Tyr Cys Thr Arg His
210 215 220

Gly Asp Tyr Pro Arg Phe Phe Asp Val Trp Gly Gln Gly Thr Leu Val
225 230 235 240

Thr Val Ser Ser

<210> SEQ ID NO 13
<211> LENGTH: 107
<212> TYPE: PRT
<213> ORGANISM: Artificial Sequence
<220> FEATURE:
<223> OTHER INFORMATION: hZ199-V2 VL

<400> SEQUENCE: 13

Glu Ile Val Leu Thr Gln Ser Pro Ala Thr Leu Ser Leu Ser Pro Gly
1 5 10 15

Glu Arg Ala Thr Met Thr Cys Ser Ala Ser Ser Ser Val Ser Ser Tyr
20 25 30

Ile Tyr Trp Tyr Gln Gln Lys Pro Gly Gln Ala Pro Arg Leu Leu Ile
35 40 45

Tyr Leu Thr Ser Asn Leu Ala Ser Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Thr Tyr Tyr Cys Gln Gln Trp Ser Gly Asn Pro Tyr
85 90 95

Thr Phe Gly Gln Gly Thr Lys Val Glu Ile Lys 100 105

<210> SEQ ID NO 14
<211> LENGTH: 244
<212> TYPE: PRT
<213> ORGANISM: Artificial Sequence
<220> FEATURE:
<223> OTHER INFORMATION: hZ199-V2 scFv

<400> SEQUENCE: 14

Glu Ile Val Leu Thr Gln Ser Pro Ala Thr Leu Ser Leu Ser Pro Gly
1 5 10 15

Glu Arg Ala Thr Met Thr Cys Ser Ala Ser Ser Ser Val Ser Ser Tyr
20 25 30

Ile Tyr Trp Tyr Gln Gln Lys Pro Gly Gln Ala Pro Arg Leu Leu Ile
35 40 45

Tyr Leu Thr Ser Asn Leu Ala Ser Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Thr Tyr Tyr Cys Gln Gln Trp Ser Gly Asn Pro Tyr
85 90 95

Thr Phe Gly Gln Gly Thr Lys Val Glu Ile Lys Gly Ser Thr Ser Gly
100 105 110

Ser Gly Lys Pro Gly Ser Gly Glu Gly Ser Thr Lys Gly Glu Val Gln
115 120 125

Leu Val Glu Ser Gly Gly Gly Leu Val Lys Pro Gly Gly Ser Leu Arg
130 135 140

Leu Ser Cys Ala Ala Ser Gly Phe Thr Phe Ser Ser Tyr Ala Met Ser
145 150 155 160

Trp Val Arg Gln Ala Pro Gly Lys Gly Leu Glu Trp Val Ala Glu Ile
165 170 175

Ser Ser Gly Gly Ser Tyr Thr Tyr Tyr Pro Asp Ser Val Lys Gly Arg
180 185 190

Phe Thr Ile Ser Arg Asp Asn Ala Lys Asn Ser Leu Tyr Leu Gln Met
195 200 205

Asn Ser Leu Arg Ala Glu Asp Thr Ala Val Tyr Tyr Cys Thr Arg His
210 215 220

Gly Asp Tyr Pro Arg Phe Phe Asp Val Trp Gly Gln Gly Thr Leu Val
225 230 235 240

Thr Val Ser Ser

<210> SEQ ID NO 15
<211> LENGTH: 732
<212> TYPE: DNA
<213> ORGANISM: Artificial Sequence
<220> FEATURE:
<223> OTHER INFORMATION: hZ199-V1

<400> SEQUENCE: 15
gaaatagtcc tgactcagtc tccggcaact ttgtctttgt cacctggaga acgcgctaca 60
atgtcctgct ccgcgtcctc tagcgtttca agctacatat actggtacca acaaaagccg 120
ggtcaagccc cgcgcctgct gatctatctc accagcaacc tcgcgtccgg tgtgcctgct 180
cgattcagcg gttctgggtc tgggacggac ttcactctca ctatttcaag cctcgaacca 240
gaggacttcg ctacttacta ttgtcagcaa tggagtggga acccgtacac gttcggacaa 300
ggaactaagc tcgagattaa aggtagtacc agcggatctg ggaagcctgg tagtggagag 360
ggcagcacaa agggtgaggt gcagttggta gaatcaggtg ggggactcgt gaaacccggc 420
ggatcattga ggctcagttg cgccgcatct ggattcacgt ttagttccta cgccatgtca 480
tgggtcaggc aagcccctgg aaaaggcctt gagtgggttg ctgaaatttc cagcgggggt 540
agctacactt actacccgga tagcgttaaa ggcagattca ctattagtag ggataacgcc 600
aagaacagtc tttacctcca gatgaattcc cttagggctg aagatacagc ggtctactac 660
tgtacaaggc acggggacta tccccgcttc ttcgatgtat ggggacaagg cacgcttgtg 720
acagtgagca gc 732

<210> SEQ ID NO 16
<211> LENGTH: 732
<212> TYPE: DNA
<213> ORGANISM: Artificial Sequence
<220> FEATURE:
<223> OTHER INFORMATION: hZ199-V2

<400> SEQUENCE: 16
gaaatagtct tgacccagtc tcccgctacc ctcagtcttt cacccggtga acgcgctacg 60
atgacgtgtt cagcatccag ctctgtgtct tcctacattt attggtacca gcagaaacca 120
ggccaagcgc cgcgcctcct catttacctt acttcaaacc ttgcatccgg tattcccgcg 180
agattcagcg gtagtggttc tggaacggat tttacactta cgattagttc acttgaaccc 240
gaagatttcg ccacgtatta ctgtcagcaa tggtcaggaa atccttacac tttcggccaa 300
ggtaccaaag tcgagatcaa agggtccact tctggttcag gtaagccagg tagtggcgag 360
gggagtacaa agggggaagt gcagctcgtc gagtcaggtg gcggacttgt aaaaccgggg 420
gggtcactcc ggctgtcctg cgcagcgagt ggatttacct ttagcagtta tgcaatgtcc 480
tgggtaagac aagctccggg caagggactg gaatgggtgg ctgaaatctc tagtggtgga 540
agttatacct actaccctga tagcgtgaag ggtagattta ctattagtcg ggacaacgct 600
aagaatagct tgtaccttca aatgaacagt ttgcgagcag aggacactgc agtttattat 660
tgcacccggc acggagatta tcctcgcttt tttgacgtat ggggacaggg aactctcgtg 720
actgttagta gc 732

<210> SEQ ID NO 17
<211> LENGTH: 25
<212> TYPE: PRT
<213> ORGANISM: Artificial Sequence
<220> FEATURE:
<223> OTHER INFORMATION: CD8alpha transmembrane domain

<400> SEQUENCE: 17

Ile Tyr Ile Trp Ala Pro Leu Ala Gly Thr Cys Gly Val Leu Leu Leu
1 5 10 15

Ser Leu Val Ile Thr Leu Tyr Cys Lys
20 25

<210> SEQ ID NO 18
<211> LENGTH: 75
<212> TYPE: DNA
<213> ORGANISM: Artificial Sequence
<220> FEATURE:
<223> OTHER INFORMATION: CD8alpha transmembrane domain

<400> SEQUENCE: 18
atctacatct gggcgccctt ggccgggact tgtggggtcc ttctcctgtc actggttatc 60 acccttact gcaaa 75

<210> SEQ ID NO 19
<211> LENGTH: 27
<212> TYPE: PRT
<213> ORGANISM: Artificial Sequence
<220> FEATURE:
<223> OTHER INFORMATION: CD28 transmembrane domain

<400> SEQUENCE: 19

Phe Trp Val Leu Val Val Val Gly Gly Val Leu Ala Cys Tyr Ser Leu
1 5 10 15

Leu Val Thr Val Ala Phe Ile Ile Phe Trp Val
20 25

<210> SEQ ID NO 20
<211> LENGTH: 81
<212> TYPE: DNA
<213> ORGANISM: Artificial Sequence
<220> FEATURE:
<223> OTHER INFORMATION: CD28 transmembrane domain

<400> SEQUENCE: 20
ttttgggtcc tcgtcgtagt tggaggggta cttgcctgtt atagcctcct ggttaccgta 60
gcatttatta tattctgggt g 81

<210> SEQ ID NO 21
<211> LENGTH: 41
<212> TYPE: PRT
<213> ORGANISM: Artificial Sequence
<220> FEATURE:
<223> OTHER INFORMATION: CD28 costimulatory domain

<400> SEQUENCE: 21

Arg Ser Lys Arg Ser Arg Leu Leu His Ser Asp Tyr Met Asn Met Thr
1 5 10 15

Pro Arg Arg Pro Gly Pro Thr Arg Lys His Tyr Gln Pro Tyr Ala Pro
20 25 30

Pro Arg Asp Phe Ala Ala Tyr Arg Ser
35 40

<210> SEQ ID NO 22
<211> LENGTH: 123
<212> TYPE: DNA
<213> ORGANISM: Artificial Sequence
<220> FEATURE:
<223> OTHER INFORMATION: CD28 costimulatory domain

<400> SEQUENCE: 22
aggagtaaga ggagcaggct cctgcacagt gactacatga acatgactcc ccgccgcccc 60
gggcccaccc gcaagcatta ccagccctat gccccaccac gcgacttcgc agcctatcgc 120
tcc 123

<210> SEQ ID NO 23
<211> LENGTH: 40
<212> TYPE: PRT
<213> ORGANISM: Artificial Sequence
<220> FEATURE:
<223> OTHER INFORMATION: 4-1BB costimulatory domain

<400> SEQUENCE: 23

Arg Gly Arg Lys Lys Leu Leu Tyr Ile Phe Lys Gln Pro Phe Met Arg

```
1               5                   10                  15

Pro Val Gln Thr Thr Gln Glu Glu Asp Gly Cys Ser Cys Arg Phe Pro
            20                  25                  30

Glu Glu Glu Glu Gly Gly Cys Glu
        35                  40


<210> SEQ ID NO 24
<211> LENGTH: 120
<212> TYPE: DNA
<213> ORGANISM: Artificial Sequence
<220> FEATURE:
<223> OTHER INFORMATION: 4-1BB costimulatory domain

<400> SEQUENCE: 24

cggggcagaa agaaactcct gtatatattc aaacaaccat ttatgagacc agtacaaact     60

actcaagagg aagatggctg tagctgccga tttccagaag aagaagaagg aggatgtgaa    120


<210> SEQ ID NO 25
<211> LENGTH: 113
<212> TYPE: PRT
<213> ORGANISM: Artificial Sequence
<220> FEATURE:
<223> OTHER INFORMATION: 4-1BB costimulatory domain

<400> SEQUENCE: 25

Leu Arg Val Lys Phe Ser Arg Ser Ala Asp Ala Pro Ala Tyr Gln Gln
1               5                   10                  15

Gly Gln Asn Gln Leu Tyr Asn Glu Leu Asn Leu Gly Arg Arg Glu Glu
            20                  25                  30

Tyr Asp Val Leu Asp Lys Arg Arg Gly Arg Asp Pro Glu Met Gly Gly
        35                  40                  45

Lys Pro Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg


<210> SEQ ID NO 26
<211> LENGTH: 339
<212> TYPE: DNA
<213> ORGANISM: Artificial Sequence
<220> FEATURE:
<223> OTHER INFORMATION: CD3zeta signaling domain

<400> SEQUENCE: 26

ctgagagtga agttcagcag gagcgcagac gcccccgcgt accagcaggg ccagaaccag     60

ctctataacg agctcaatct aggacgaaga gaggagtacg atgttttgga caagagacgt    120

ggccgggacc ctgagatggg gggaaagccg agaaggaaga accctcagga aggcctgtac    180

aatgaactgc agaaagataa gatggcggag gcctacagtg agattgggat gaaaggcgag    240

cgccggaggg gcaaggggca cgatggcctt taccagggtc tcagtacagc caccaaggac    300

acctacgacg cccttcacat gcaggccctg ccccctcgc                           339


<210> SEQ ID NO 27
```

<211> LENGTH: 114
<212> TYPE: PRT
<213> ORGANISM: Artificial Sequence
<220> FEATURE:
<223> OTHER INFORMATION: CD3zeta signaling domain

<400> SEQUENCE: 27

Leu Arg Val Lys Phe Ser Arg Ser Ala Asp Ala Pro Ala Tyr Gln Gln
1               5                   10                  15

Gly Gln Asn Gln Leu Phe Asn Glu Leu Asn Leu Gly Arg Arg Glu Glu
            20                  25                  30

Phe Asp Val Leu Asp Lys Arg Arg Gly Arg Asp Pro Glu Met Gly Gly
        35                  40                  45

Lys Pro Gln Arg Arg Lys Asn Pro Gln Glu Gly Leu Tyr Asn Glu Leu
    50                  55                  60

Gln Lys Asp Lys Met Ala Glu Ala Tyr Ser Glu Ile Gly Met Lys Gly
65                  70                  75                  80

Glu Arg Arg Arg Gly Lys Gly His Asp Gly Leu Phe Gln Gly Leu Ser
                85                  90                  95

Thr Ala Thr Lys Asp Thr Phe Asp Ala Leu His Met Gln Ala Leu Pro
            100                 105                 110

Pro Arg

<210> SEQ ID NO 28
<211> LENGTH: 342
<212> TYPE: DNA
<213> ORGANISM: Artificial Sequence
<220> FEATURE:
<223> OTHER INFORMATION: CD3zeta signaling domain

<400> SEQUENCE: 28
ctgagagtga agttcagcag gagcgcagac gcccccgcgt accagcaggg ccagaaccag 60
ctctttaacg agctcaatct aggacgaaga gaggagttcg atgttttgga caagagacgt 120
ggccgggacc ctgagatggg gggaaagccg cagagaagga agaaccctca ggaaggcctg 180
tacaatgaac tgcagaaaga taagatggcg gaggcctaca gtgagattgg gatgaaaggc 240
gagcgccgga ggggcaaggg gcacgatggc ctttttccagg gtctcagtac agccaccaag 300
gacacctttg acgcccttca catgcaggcc ctgccccctc gc 342

<210> SEQ ID NO 29
<211> LENGTH: 20
<212> TYPE: PRT
<213> ORGANISM: Artificial Sequence
<220> FEATURE:
<223> OTHER INFORMATION: B2M signal peptide

<400> SEQUENCE: 29

Met Ser Arg Ser Val Ala Leu Ala Val Leu Ala Leu Leu Ser Leu Ser
1               5                   10                  15

Gly Leu Glu Ala
            20

<210> SEQ ID NO 30
<211> LENGTH: 60
<212> TYPE: DNA
<213> ORGANISM: Artificial Sequence
<220> FEATURE:
<223> OTHER INFORMATION: B2M signal peptide

<400> SEQUENCE: 30
atgtcccgct ctgttgcttt ggctgtgctg gcccttttgt cccttagcgg actggaggcc 60

<210> SEQ ID NO 31
<211> LENGTH: 21
<212> TYPE: PRT
<213> ORGANISM: Artificial Sequence
<220> FEATURE:
<223> OTHER INFORMATION: CD8alpha signal peptide

<400> SEQUENCE: 31

Met Ala Leu Pro Val Thr Ala Leu Leu Leu Pro Leu Ala Leu Leu Leu
1 5 10 15

His Ala Ala Arg Pro
20

<210> SEQ ID NO 32
<211> LENGTH: 63
<212> TYPE: DNA
<213> ORGANISM: Artificial Sequence
<220> FEATURE:
<223> OTHER INFORMATION: CD8alpha signal peptide

<400> SEQUENCE: 32
atggccttac cagtgaccgc cttgctcctg ccgctggcct tgctgctcca cgccgccagg 60
ccg 63

<210> SEQ ID NO 33
<211> LENGTH: 45
<212> TYPE: PRT
<213> ORGANISM: Artificial Sequence
<220> FEATURE:
<223> OTHER INFORMATION: CD8alpha hinge region

<400> SEQUENCE: 33

Thr Thr Thr Pro Ala Pro Arg Pro Pro Thr Pro Ala Pro Thr Ile Ala
1 5 10 15

Ser Gln Pro Leu Ser Leu Arg Pro Glu Ala Cys Arg Pro Ala Ala Gly
20 25 30

Gly Ala Val His Thr Arg Gly Leu Asp Phe Ala Cys Asp
35 40 45

<210> SEQ ID NO 34
<211> LENGTH: 135
<212> TYPE: DNA
<213> ORGANISM: Artificial Sequence
<220> FEATURE:
<223> OTHER INFORMATION: CD8alpha hinge region

<400> SEQUENCE: 34
accacgacgc cagcgccgcg accaccaaca ccggcgccca ccatcgcgtc gcagcccctg 60
tccctgcgcc cagaggcgtg ccggccagcg gcggggggcg cagtgcacac gagggggctg 120
gacttcgcct gtgat 135

<210> SEQ ID NO 35
<211> LENGTH: 39
<212> TYPE: PRT
<213> ORGANISM: Artificial Sequence
<220> FEATURE:
<223> OTHER INFORMATION: CD28 hinge region

<400> SEQUENCE: 35

Ile Glu Val Met Tyr Pro Pro Pro Tyr Leu Asp Asn Glu Lys Ser Asn
1 5 10 15

-continued

```
Gly Thr Ile Ile His Val Lys Gly Lys His Leu Cys Pro Ser Pro Leu
            20                  25                  30

Phe Pro Gly Pro Ser Lys Pro
        35


<210> SEQ ID NO 36
<211> LENGTH: 117
<212> TYPE: DNA
<213> ORGANISM: Artificial Sequence
<220> FEATURE:
<223> OTHER INFORMATION: CD28 hinge region

<400> SEQUENCE: 36

attgaagtta tgtatcctcc tccttaccta gacaatgaga agagcaatgg aaccattatc      60

catgtgaaag ggaaacacct ttgtccaagt cccctatttc ccggaccttc taagccc        117


<210> SEQ ID NO 37
<211> LENGTH: 12
<212> TYPE: PRT
<213> ORGANISM: Artificial Sequence
<220> FEATURE:
<223> OTHER INFORMATION: IgG4 hinge region

<400> SEQUENCE: 37

Glu Ser Lys Tyr Gly Pro Pro Cys Pro Pro Cys Pro
1               5                   10


<210> SEQ ID NO 38
<211> LENGTH: 36
<212> TYPE: DNA
<213> ORGANISM: Artificial Sequence
<220> FEATURE:
<223> OTHER INFORMATION: IgG4 hinge region

<400> SEQUENCE: 38

gaaagcaaat acgggccgcc gtgtccaccc tgtccg                                36
```

NKG2A-TARGETING ANTIBODY AND USE THEREOF

RELATED APPLICATIONS

This application is a United States National Stage Application filed under 35 U.S.C. § 371 of PCT Patent Application Serial No. PCT/CN2021/131435, filed Nov. 18, 2021, which claims priority to Chinese Patent Application Serial No. CN 202011320557.5, filed Nov. 23, 2020, the disclosure of all of which are hereby incorporated by reference in their entirety.

TECHNICAL FIELD

The present disclosure belongs to the field of immunotherapy. More specifically, the present disclosure relates to a NKG2A-targeting antibody and use thereof in the prevention and/or treatment and/or diagnosis of diseases.

BACKGROUND ART

Natural killer (NK) cells are a very important type of lymphocytes in the body, which play an important role in both innate immunity and acquired immunity. There are two types of surface receptors on the surface of NK cells, which can be divided into inhibitory receptor and activating receptor according to the their function. They mediate different recognition modes of NK cells and transmit different inhibitory signals and activating signals, respectively. The CD94/NKG2 family is a type of receptor family that has been studied more, mainly including NKG2A, NKG2B, NKG2C, NKG2D, NKG2E, NKG2F, NKG2H and other members. Among them, NKG2A is an inhibitory receptor, and its ligand is the non-classical major histocompatibility complex class I molecule HLA-E. After the HLA-E molecules expressed on the target cells bind with NKG2A, the killing function of NK cells is inhibited. Therefore, antibodies targeting CD94/ NKG2A may enhance the killing activity of tumor-specific lymphocytes against tumor cells.

Various anti-NKG2A antibodies have been described in the art. For example, Sivori et al. (Eur J Immunol 1996; 26:2487-92) mention the murine anti-NKG2A antibody Z270; Carretero et al. (EurJ Immunol 1997; 27:563-7) describe the murine anti-NKG2A antibody Z199 (now commercially available from Beckman Coulter, Inc., product number IM2750, USA); Vance et al. (J Exp Med 1999; 190:1801-12) mention the rat anti-mouse NKG2-antibody 20D5 (now commercially available from BD Biosciences Pharmingen, Cat. No. 550518, USA); and US Patent Application 20030095965 describes the murine antibody 3S9, which reportedly binds to NKG2A, NKG2C and NKG2E.

The present disclosure aims to provide a NKG2A-targeting antibody and use thereof in the prevention and/or treatment and/or diagnosis of diseases.

SUMMARY

In a first aspect, the present disclosure provides a NKG2A-targeting antibody, comprising a light chain variable region and a heavy chain variable region, wherein the light chain variable region comprises CDR-L1 as set forth in SEQ ID NO: 1, CDR-L2 as set forth in SEQ ID NO: 2, and CDR-L3 as set forth in SEQ ID NO: 3, and the heavy chain variable region comprises CDR-H1 as set forth in SEQ ID NO: 4, CDR-H2 as set forth in SEQ ID NO: 5, and CDR-H3 as set forth in SEQ ID NO: 6, wherein the light chain variable region comprises amino acid M at position 21, and amino acid T at position 85, and the heavy chain variable region comprises amino acid M at position 34, amino acid A at position 49, amino acid P at position 61, and amino acid T at position 97.

In an embodiment, the light chain variable region comprises amino acid S or T at position 22, amino acid I or V at position 58, and amino acid L or V at position 104.

In a preferred embodiment, the light chain variable region of the anti-NKG2A antibody has at least 90% identity to an amino acid sequence selected from the group consisting of SEQ ID NOs: 10 and 13, or has one or several (e.g., 2, 3, 4, 5, 6, 7, 8, 9, 10, at most 7, at most 6, at most 5, at most 4, at most 3, at most 2) conservative modifications of amino acids compared to SEQ ID NO: 10 or 13, the heavy chain variable region has at least 90% identity to the amino acid sequence as set forth in SEQ ID NO: 11 or has one or several (e.g., 2, 3, 4, 5, 6, 7, 8, 9, 10, at most 7, at most 6, at most 5, at most 4, at most 3, at most 2) conservative modifications of amino acids compared to the amino acid sequence as set forth in SEQ ID NO: 11. More preferably, the anti-NKG2A antibody comprises a light chain variable region selected from the group consisting of SEQ ID NOs: 10 and 13 and a heavy chain variable region as set forth in SEQ ID NO: 11.

In an embodiment, the anti-NKG2A antibody has an amino acid sequence selected from the group consisting of SEQ ID NOs: 12 and 14.

The present disclosure further provides a nucleic acid molecule encoding the anti-NKG2A antibody as described above. Therefore, in an embodiment, the nucleic acid molecule encoding the anti-NKG2A antibody has at least 90%, at least 91%, at least 92%, at least 93%, at least 94%, at least 95%, at least 96%, at least 97%, at least 98%, at least 99%, or 100% sequence identity to a nucleotide sequence selected from the group consisting of SEQ ID NOs: 16-17, and the anti-NKG2A antibody encoded thereby can specifically bind to NKG2A. Preferably, the nucleic acid molecule encoding the anti-NKG2A antibody is selected form SEQ ID NOs: 16-17.

In another aspect, the present disclosure further provides a multispecific antibody (preferably bispecific antibody or trispecific antibody), which comprises the anti-NKG2A antibody as described above, and one or more second antibodies or antigen-binding portions thereof that specifically bind to antigens different from NKG2A.

In an embodiment, the second antibody or antigen-binding portion thereof may be in the form of any antibody or antibody fragment, such as a full-length antibody, Fab, Fab', (Fab')2, Fv, scFv, scFv-scFv, a minibody, a diabody or sdAb.

The present disclosure further provides a vector comprising a nucleic acid molecule encoding the anti-NKG2A antibody or the multispecific antibody as described above, and a host cell expressing the anti-NKG2A antibody or the multispecific antibody.

In another aspect, the present disclosure further provides a chimeric receptor comprising one or more NK inhibitory ligands, a transmembrane domain and a signaling domain, wherein the NK inhibitory ligand comprises the anti-NKG2A antibody or the multispecific antibody comprising the anti-NKG2A antibody as described above, wherein the signaling domain comprises one or more co-stimulatory domains.

In an embodiment, the chimeric receptor comprises two NK inhibitory ligands, wherein the first NK inhibitory ligand is the anti-NKG2A antibody as described above and the second NK inhibitory ligand is selected from: (1) an antibody or a fragment thereof targeting one of the following NK inhibitory receptors: LIR1, NKG2B, CD94, LIR2, LIR3, KIR2DL1, KIR2DL2/3, KIR3DL1, CEACAM1, LAIR1, and KLRG1; or (2) HLA-E, HLA-F, HLA-G, cadherin, collagen, OCIL, sialic acid, PD-L1, PD-L2, CD155, CD112, CD113, Gal-9, FGL1, and NK inhibitory receptor binding regions comprised therein.

In an embodiment, the signaling domain of the chimeric receptor of the disclosure consists of one or more co-stimulatory domains. That is, it does not comprise a primary signaling domain, such as that from FcRγ, FcRβ, CD3γ, CD3δ, CD3ε, CD3ζ, CD22, CD79a, CD79b and CD66d.

In another embodiment, the signaling domain of the chimeric receptor of the present disclosure may further comprise a primary signaling domain, such as the CD3ζ intracellular region.

The present disclosure further provides a nucleic acid molecule encoding the NKG2A-targeting chimeric receptor as defined above, and a vector comprising the nucleic acid molecule.

The present disclosure further provides an engineered immune cell, which expresses the chimeric receptor comprising the anti-NKG2A antibody of the present disclosure, wherein the expression of at least one MHC-related gene is suppressed or silenced.

In an embodiment, the MHC-related gene is selected from the group consisting of: HLA-A, HLA-B, HLA-C, B2M, HLA-DPA, HLA-DQ, HLA-DRA, TAP1, TAP2, LMP2, LMP7, RFX5, RFXAP, RFXANK, CIITA and a combination thereof, and preferably selected from the group consisting of HLA-A, HLA-B, HLA-C, B2M, RFX5, RFXAP, RFXANK, CIITA and a combination thereof.

In an embodiment, the engineered immune cell expressing the chimeric receptor comprising the anti-NKG2A antibody of the present disclosure further comprises suppressed or silenced expression of at least one TCR/CD3 gene, examples of which include TRAC, TRBC, CD3γ, CD3δ, CD3ε, CD3ζ.

In an embodiment, the engineered immune cell provided by the present disclosure further express a chimeric antigen receptor targeting a tumor antigen.

In an embodiment, the immune cell is selected from the group consisting of a T cell, a NK cell, a NKT cell, a macrophage, and a dendritic cell.

In another aspect, the present disclosure further provides an antibody conjugate comprising the anti-NKG2A antibody as defined herein and a second functional structure, wherein the second functional structure is selected from the group consisting of an Fc, a radioisotope, a structure moiety for extending half-life, a detectable marker and a drug.

In an embodiment, the structure moiety for extending half-life is selected from the group consisting of an albumin-binding structure, a transferrin-binding structure, a polyethylene glycol molecule, a recombinant polyethylene glycol molecule, a human serum albumin, a fragment of human serum albumin, and a polypeptide (including an antibody) binding to human serum albumin. In an embodiment, the detectable marker is selected from the group consisting of a fluorophore, a chemiluminescent compound, a bioluminescent compound, an enzyme, an antibiotic resistance gene, and a contrast agent. In an embodiment, the drug is selected from the group consisting of a cytotoxin and an immunomodulator.

In another aspect, the present disclosure further provides a detection kit comprising the antibody, the multispecific antibody, the antibody conjugate or the chimeric receptor described in the present disclosure.

In another aspect, the present disclosure further provides a pharmaceutical composition comprising the antibody, the chimeric receptor, the multispecific antibody, the engineered cell or the antibody conjugate described in the present disclosure, and one or more pharmaceutically acceptable excipients.

In another aspect, the present disclosure further provides a method for treating and/or preventing and/or diagnosing diseases associated with NKG2A expression, comprising administering to a subject the antibody, the chimeric receptor, the multispecific antibody, the antibody conjugate, the engineered immune cell or the pharmaceutical composition as described above.

DETAILED DESCRIPTION

Figure 1:
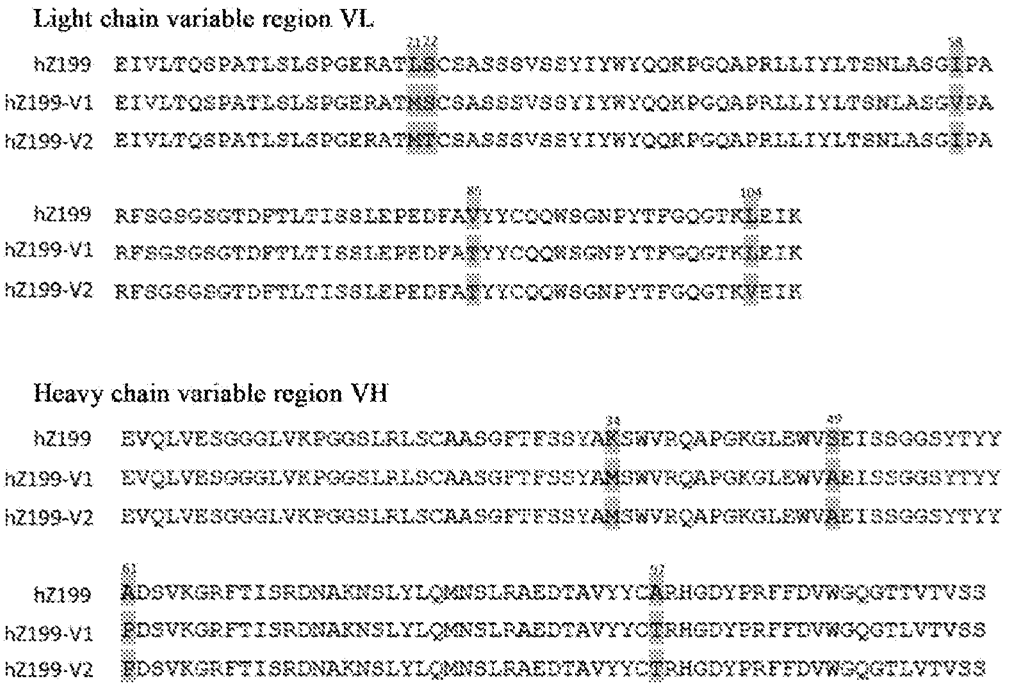
FIG. 1 shows the sequence alignment results of the light chain variable region and the heavy chain variable region of hZ199 and its back mutant antibodies hZ199-V1 and hZ199-V2. The amino acid site of the back mutation is highlighted in gray, and the number shows the position of the mutation site in the light chain variable region and the heavy chain variable region.

Unless otherwise specified, all scientific and technical terms used herein have the same meaning as commonly understood by one of ordinary skill in the art to which this disclosure belongs.

Anti-NKG2A Antibody

In the context of the present disclosure, the "Z199 antibody" is the murine anti-NKG2A antibody Z199 as described by Carretero et al. (Eur J Immunol 1997; 27:563-7), now commercially available from Beckman Coulter, Inc., Product No. IM2750. "hZ199 antibody" refers to a humanized Z199 antibody, which comprises a light chain variable region as set forth in SEQ ID NO: 7, a heavy chain variable region as set forth in SEQ ID NO: 8, with the full-length amino acid sequence as set forth in SEQ ID NO: ID NO: 9.

The new NKG2A antibody provided by the present disclosure is obtained by back mutation based on hZ199, so as to provide an antibody with higher affinity and better effect of inhibiting NK cell killing.

As used herein, the term "antibody" has the broadest meaning understood by those skilled in the art and includes monoclonal antibodies (including whole antibodies), polyclonal antibodies, multivalent antibodies, multispecific antibodies (e.g., bispecific antibodies), and antibody fragments or synthetic polypeptides carrying one or more CDR sequences capable of exhibiting the desired biological activity. The antibodies of the present disclosure may be of any class (e.g., IgG, IgE, IgM, IgD, IgA, etc.) or subclass (e.g., IgG1, IgG2, IgG2a, IgG3, IgG4, IgA1, IgA2, etc.).

Typically, whole antibodies comprise two heavy chains and two light chains disulfide-bonded together, each light chain being disulfide-bonded to a respective heavy chain, to form a "Y" configuration. Each heavy chain comprises a heavy chain variable region (VH) and a heavy chain constant region, wherein the heavy chain variable region comprises three complementarity determining regions (CDRs):

CDR-H1, CDR-H2 and CDR-H3, and the heavy chain constant region comprises three constant domains: CH1, CH2 and CH3. Each light chain comprises a light chain variable region (VL) and a light chain constant region, wherein the light chain variable region comprises three CDRs: CDR-L1, CDR-L2 and CDR-L3, and the light chain constant region comprises a constant domain CL. In the heavy/light chain variable regions, the CDRs are separated by more conserved framework regions (FRs). The heavy/light chain variable regions are responsible for the recognition and binding of the antigen, while the constant regions mediates the binding of the antibody to host tissues or factors, including various cells of the immune system (e.g., effector cells) and the first component of the classical complement system.

The precise amino acid sequence boundaries for a given CDR or FR can be readily determined using a number of numbering schemes well known in the art, including: Kabat et al. (1991), "Sequences of Proteins of Immunological Interest," 5th Edition, Public Health Service, National Institutes of Health, Bethesda, MD ("Kabat" numbering scheme); Al-Lazikani et al., (1997) JMB 273, 927-948 ("Chothia" numbering scheme); MacCallum et al., J. Mol. Biol 262:732-745 (1996), "Antibody-antigen interactions: Contact analysis and binding sitetopography," J. Mol. Biol. 262, 732-745" ("Contact" numbering scheme); Lefranc M P et al., "IMGT unique numbering for immunoglobulin and T cell receptor variable domains and Ig superfamily V-like domains," Dev Comp Immunol, 2003 January; 27 (1):55-77 ("IMGT" numbering scheme); Honegger A and Plückthun A, "Yet another numbering scheme for immunoglobulin variable domains: an automatic modeling and analysis tool," JMol Biol, 2001 Jun. 8; 309 (3):657-70 ("Aho" numbering scheme); and Martin et al., "Modeling antibody hypervariable loops: a combined algorithm," PNAS, 1989, 86 (23): 9268-9272 ("AbM" numbering scheme).

The boundaries of a given CDR or FR may vary depending on the scheme used for identification. For example, the Kabat scheme is based on structural alignment, while the Chothia scheme is based on structural information. Both the Kabat and Chothia numbering schemes are based on the sequence length of the most common antibody regions and place certain insertions and deletions ("indels") at different positions, resulting in different numbering. The Contact scheme is based on the analysis of complex crystal structures and is similar in many respects to the Chothia numbering scheme. The AbM scheme is a compromise between the Kabat and Chothia definitions and is based on the scheme used by the AbM antibody modeling software of Oxford Molecular.

Thus, unless otherwise specified, a "CDR" of a given antibody or region thereof (e.g., variable region thereof) is understood to encompass the CDRs defined by any of the above schemes or other known schemes. For example, where it is specified that a particular CDR (e.g., CDR3) contains a given amino acid sequence, it is understood that such a CDR may also have the sequence of the corresponding CDR (e.g., CDR3) as defined by any of the above schemes or other known schemes. Likewise, unless otherwise specified, FRs for a given antibody or region thereof (e.g., variable region thereof) are understood to encompass FRs as defined by any of the above schemes or other known schemes Amino acid numbering herein follows the Chothia scheme unless otherwise indicated.

As used herein, the term "antibody fragment" or "antigen-binding portion" comprises only a portion of an intact antibody, and typically comprises the antigen-binding site of the intact antibody and thus retains the ability to bind antigen. Examples of antibody fragments of the present disclosure include, but are not limited to: Fab, Fab', F(ab')2, Fd fragment, Fd', Fv fragment, scFv, disulfide-linked Fv (sdFv), antibody heavy chain variable region (VH) or light chain variable region (VL), linear antibody, "diabody" with two antigen binding sites, single domain antibody, nanobody, a natural ligand for the antigen or a functional fragment thereof. Accordingly, an "antibody" of the present disclosure encompasses antibody fragments as defined above.

"Single-chain antibody" and "scFv" are used interchangeably herein and refer to an antibody formed by linking the heavy chain variable region (VH) and the light chain variable region (VL) of an antibody through a linker. The optimal length and/or amino acid composition of the linker can be selected. The length of the linker may significantly affect the folding and interaction of the variable domain of scFv. In fact, if shorter linkers (e.g., with between 5-10 amino acids) are used, intrachain folding may be prevented. For selection of linker size and composition, see, e.g., Hollinger et al., 1993 Proc Natl Acad. Sci. U.S.A. 90:6444-6448; U.S. Patent Application Publication Nos. 2005/0100543, 2005/0175606, 2007/0014794 and PCT Publication Nos. WO2006/020258 and WO2007/024715, the entire contents of which are incorporated herein by reference. A scFv may comprise VH and VL linked in any order, e.g. VH-linker-VL or VL-linker-VH.

In a first aspect, the present disclosure provides a NKG2A-targeting antibody, comprising a light chain variable region and a heavy chain variable region, wherein the light chain variable region comprises CDR-L1 as set forth in SEQ ID NO: 1, CDR-L2 as set forth in SEQ ID NO: 2, and CDR-L3 as set forth in SEQ ID NO: 3, and the heavy chain variable region comprises CDR-H1 as set forth in SEQ ID NO: 4, CDR-H2 as set forth in SEQ ID NO: 5, and CDR-H3 as set forth in SEQ ID NO: 6, wherein the light chain variable region comprises amino acid M at position 21, and amino acid T at position 85, and the heavy chain variable region comprises amino acid M at position 34, amino acid A at position 49, amino acid P at position 61, and amino acid T at position 97.

In an embodiment, the light chain variable region comprises amino acid S or T at position 22, amino acid I or V at position 58, and amino acid L or V at position 104.

In a preferred embodiment, the light chain variable region of the anti-NKG2A antibody has at least 90% identity to an amino acid sequence selected from the group consisting of SEQ ID NOs: 10 and 13, or has one or several (e.g., 2, 3, 4, 5, 6, 7, 8, 9, 10, at most 7, at most 6, at most 5, at most 4, at most 3, at most 2) conservative modifications of amino acids compared to SEQ ID NO: 10 or 13, the heavy chain variable region has at least 90% identity to the amino acid sequence as set forth in SEQ ID NO: 11 or has one or several (e.g., 2, 3, 4, 5, 6, 7, 8, 9, 10, at most 7, at most 6, at most 5, at most 4, at most 3, at most 2) conservative modifications of amino acids compared to SEQ ID NO: 11. More preferably, the anti-NKG2A antibody comprises a light chain variable region selected from the group consisting of SEQ ID NO: 10 and 13 and a heavy chain variable region as set forth in SEQ ID NO: 11.

In an embodiment, the anti-NKG2A antibody has an amino acid sequence selected from the group consisting of SEQ ID NOs: 12 and 14.

As used herein, the term "sequence identity" means the degree to which two (nucleotide or amino acid) sequences in alignment have the same residue at the same position, and is usually expressed as a percentage. Preferably, identity is determined over the entire length of the sequences being compared. Therefore, two copies of the exact same sequence have 100% identity. Those skilled in the art know that several algorithms can be used to determine sequence identity, such as Blast (Altschul et al. (1997) Nucleic Acids Res. 25:3389-3402), Blast2 (Altschul et al. (1990) J. Mol. Biol. 215: 403-410), Smith-Waterman (Smith et al. (1981) J. Mol. Biol. 147:195-197) and Clustal W.

As used herein, the term "conservative modification" refers to an amino acid modification that does not significantly affect or alter the binding characteristics of an antibody or antibody fragment comprising the amino acid sequence. These conservative modifications include amino acid substitutions, additions and deletions. Modifications can be introduced into the antibodies of the present disclosure by standard techniques known in the art, such as site-directed mutagenesis and PCR-mediated mutagenesis. A conservative amino acid substitution is one in which an amino acid residue is replaced by an amino acid residue with a similar side chain Families of amino acid residues with similar side chains have been defined in the art and include those with basic side chain (e.g., lysine, arginine, histidine), acidic side chain (e.g., aspartic acid, glutamic acid), uncharged polar side chain (e.g., glycine, asparagine, glutamine, serine, threonine, tyrosine, cysteine), non-polar side chain (e.g., alanine, valine, leucine, isoleucine, proline, phenylalanine, methionine, tryptophan), beta-branched side chain (e.g., threonine, valine, isoleucine) and aromatic side chain (e.g., tyrosine, phenylalanine, tryptophan, histidine). Conservative modifications can be selected, for example, on the basis of similarity in polarity, charge, solubility, hydrophobicity, hydrophilicity, and/or the amphipathic nature of the residues involved.

In an aspect, the present disclosure further provides a multispecific antibody (preferably a bispecific antibody or a trispecific antibody) comprising the anti-NKG2A antibody as described above, and one or more second antibodies that specifically bind to antigens different from NKG2A.

As used herein, the term "multispecific" means that the antigen binding protein has polyepitopic specificity (i.e., is capable of specifically binding two, three or more different epitopes on one biomolecule or is capable of specifically binding epitopes on two, three or more different biomolecules). As used herein, the term "bispecific" means that an antigen binding protein has two different antigen binding specificities.

In an embodiment, the second antibody may be in the form of any antibody or antibody fragment, such as a full-length antibody, Fab, Fab', (Fab')2, Fv, scFv, scFv-scFv, a minibody, a diabody or sdAb.

Nucleic Acid, Vector, Host Cell

In another aspect, the present disclosure relates to a nucleic acid molecule encoding the anti-NKG2A antibody or multispecific antibody of the present disclosure. The nucleic acid of the present disclosure may be RNA, DNA or cDNA. According to an embodiment of the present disclosure, the nucleic acid of the present disclosure is a substantially isolated nucleic acid.

In an embodiment, the nucleic acid molecule encoding the anti-NKG2A antibody has at least 90%, at least 91%, at least 92%, at least 93%, at least 94%, at least 95%, at least 96%, at least 97%, at least 98%, at least 99%, or 100% sequence identity to a nucleotide sequence selected from the group consisting of SEQ ID NOs: 16-17, and the anti-NKG2A antibody encoded thereby specifically binds NKG2A. Preferably, the nucleic acid molecule encoding the anti-NKG2A antibody is as set forth in SEQ ID NOs: 16-17.

The nucleic acid of the present disclosure may also be in the form of a vector, may be present in a vector and/or may be part of a vector, such as a plasmid, cosmid or YAC. The vector may especially be an expression vector, i.e., a vector providing for expression of the anti-NKG2A antibody in vitro and/or in vivo (i.e., in a suitable host cell, host organism and/or expression system). The expression vector typically comprises at least one nucleic acid molecule of the present disclosure operably linked to one or more suitable expression regulatory elements (e.g., promoter, enhancer, terminator, etc.). Selection of such regulatory elements and their sequences for expression in a particular host is well known to those skilled in the art. Specific examples of regulatory elements and other elements useful or necessary for expression of the anti-NKG2A antibody of the present disclosure include, but are not limited to, promoter, enhancer, terminator, integrator, selectable marker, leader sequence, reporter gene.

In another aspect, the present disclosure further provides a host cell expressing the anti-NKG2A antibody, the multispecific antibody of the present disclosure and/or a host cell containing the nucleic acid or vector of the present disclosure. Preferred host cells of the present disclosure are bacterial cells, fungal cells or mammalian cells.

Suitable bacterial cells include cells of Gram-negative bacterial strains (e.g., *Escherichia coli* strains, *Proteus* strains, and *Pseudomonas* strains) and Gram-positive bacterial strains (e.g., *Bacillus* strains, *Streptomyces* strains, *Staphylococcus* strains and *Lactococcus* strains).

Suitable fungal cells include cells of species of *Trichoderma, Neurospora*, and *Aspergillus*; or cells of species of *Saccharomyces* (e.g., *Saccharomyces cerevisiae*), *Schizosaccharomyces* (e.g., *Schizosaccharomyces pombe*), *Pichia* (e.g., *Pichia pastoris* and *Pichia methanolica*) and *Hansenula.*

Suitable mammalian cells include, for example, HEK293 cells, CHO cells, BHK cells, HeLa cells, COS cells, and the like.

However, amphibian cells, insect cells, plant cells, and any other cells known in the art for expressing heterologous proteins can also be used in the present disclosure.

Chimeric Receptor

In another aspect, the present disclosure further provides a chimeric receptor comprising the anti-NKG2A antibody as described above. Since NKG2A is a NK inhibitory receptor, chimeric receptors comprising the NKG2A antibodies can be used to inhibit the killing effect of NK cells.

In an embodiment, the present disclosure provides a chimeric receptor comprising one or more NK inhibitory ligands, a transmembrane domain and a signaling domain, wherein the NK inhibitory ligand comprises the anti-NKG2A antibody or the multispecific antibody comprising the anti-NKG2A antibody as described above, wherein the signaling domain comprises one or more co-stimulatory domains.

In an embodiment, the chimeric receptor comprises multiple NK inhibitory ligands, such as two NK inhibitory ligands, wherein the first NK inhibitory ligand is the anti-NKG2A antibody as described above, the second NK inhibitory ligand is an antibody or fragment thereof targeting other NK inhibitory receptors, and/or natural ligands of other NK inhibitory receptors or NK inhibitory receptor binding regions comprised therein.

In an embodiment, the second NK inhibitory ligand is an antibody or fragment thereof targeting a NK inhibitory receptor selected from the group consisting of a NKG2/CD94 component (e.g., NKG2B, CD94); a member of the killer cell Ig-like receptor (KIR) family (e.g., KIR2DL1, KIR2DL2/3, KIR2DL5A, KIR2DL5B, KIR3DL1, KIR3DL2, and KIR3DL3); a member of the leukocyte Ig-like receptor (LIR) family (e.g., LIR1, LIR2, LIR3, LIR5, and LIR8); a member of the NK cell receptor protein 1 (NKR-P1) family (e.g., NKR-P1B and NKR-P1D); an immune checkpoint receptor (e.g., PD-1, TIGIT, and CD96, TIM3, LAG3); carcinoembryonic antigen-related cell adhesion molecule 1 (CEACAM1); a member of the sialic acid-binding immunoglobulin-like lectin (SIGLEC) family (e.g., SIGLEC7 and SIGLEC9); leukocyte-associated immunoglobulin-like receptor 1 (LAIR1); a member of the Ly49 family (e.g., Ly49A, Ly49C, Ly49F, Ly49G1 and Ly49G4) and killer cell lectin-like receptor G1 (KLRG1). Preferably, the second NK inhibitory ligand is selected from an antibody or fragment thereof targeting a NK inhibitory receptor selected from the group consisting of: NKG2B, CD94, LIR1, LIR2, LIR3, KIR2DL1, KIR2DL2/3, KIR3DL1, CEACAM1, LAIR1 and KLRG1. Still more preferably, the second NK inhibitory ligand is an antibody or fragment thereof targeting a NK inhibitory receptor selected from the group consisting of: CD94, KIR2DL1, KIR2DL2/3, KIR3DL1, CEACAM1, LIR1, LAIR1, and KLRG1.

In an embodiment, the second NK inhibitory ligand is a natural ligand of other NK inhibitory receptors or a NK inhibitory receptor binding region comprised thereof, such as HLA-E, HLA-F, HLA-G, cadherin, collagen, OCIL, sialic acid, an immune checkpoint ligand (e.g., PD-L1/ PD-L2, CD155, CD112, CD113, Gal-9, FGL1, etc.), and a NK inhibitory receptor binding region comprised thereof. Preferably, the second NK inhibitory ligand is selected from the group consisting of HLA-E, HLA-F, HLA-G, cadherin, PD-L1, PD-L2, and a NK inhibitory receptor binding region comprised thereof. More preferably, the second NK inhibitory ligand is selected from the group consisting of a HLA-E extracellular region, a HLA-G extracellular region, an E-cadherin extracellular region, a PD-L1 extracellular region and a PD-L2 extracellular region. More preferably, the second NK inhibitory ligand is an E-cadherin extracellular region comprising EC1 and EC2, more preferably comprising EC1, EC2, EC3, EC4 and EC5.

As used herein, the term "transmembrane domain" refers to a polypeptide structure that enables expression of a chimeric receptor on the surface of an immune cell (e.g., a lymphocyte, an NK cell, or an NKT cell), and guides a cellular response of the immune cell against the target cell. The transmembrane domain may be natural or synthetic, and also may be derived from any membrane-bound protein or transmembrane protein. The transmembrane domain is capable of signaling when the chimeric receptor binds to the target antigen. The transmembrane domains particularly suitable for use in the present disclosure may be derived from, for example, a TCRα chain, a TCRβ chain, a TCRγ chain, a TCRδ chain, a CD3ζ subunit, a CD3ε subunit, a CD3γ subunit, a CD3δ subunit, CD45, CD4, CD5, CD8α, CD9, CD16, CD22, CD33, CD28, CD37, CD64, CD80, CD86, CD134, CD137, CD154, and functional fragments thereof. Alternatively, the transmembrane domain may be synthesized and may mainly contain hydrophobic residues such as leucine and valine. Preferably, the transmembrane domain is derived from CD8α chain or CD28, and has at least 70%, preferably at least 80%, more preferably at least 90%, at least 95%, at least 97% or at least 99% or 100% sequence identity to the amino acid sequence as set forth in SEQ ID NO: 17 or 19, or the encoding sequence thereof has at least 70%, preferably at least 80%, more preferably at least 90%, at least 95%, at least 97% or at least 99% or 100% sequence identity to the nucleic acid molecule as set forth in SEQ ID NO: 18 or 20.

As used herein, the term "co-stimulatory domain" refers to an intracellular functional signaling domain from a co-stimulatory molecule, which comprises the entire intracellular portion of the co-stimulatory molecule, or a functional fragment thereof. A "costimulatory molecule" refers to a cognate binding partner that specifically binds to a costimulatory ligand on a T cell, thereby mediating a costimulatory response (e.g., proliferation) of the T cell. Costimulatory molecules include, but are not limited to, MHC class 1 molecules, BTLA, and Toll ligand receptors. Examples of costimulatory domains of the present disclosure include, but are not limited to, intracellular regions derived from the following proteins: TLR1, TLR2, TLR3, TLR4, TLR5, TLR6, TLR7, TLR8, TLR9, TLR10, CARD11, CD2, CD7, CD8, CD18 (LFA-1), CD27, CD28, CD30, CD40, CD54 (ICAM), CD83, CD134 (OX40), CD137 (4-1BB), CD270 (HVEM), CD272 (BTLA), CD276 (B7-H3), CD278 (ICOS), CD357 (GITR), DAP10, LAT, NKG2C, SLP76, PD-1, LIGHT, TRIM, and ZAP70. Preferably, the costimulatory domain of the CAR of the present disclosure is from 4-1BB, CD28 or 4-1BB+CD28. In an embodiment, the 4-1BB co-stimulatory domain has at least 70%, preferably at least 80%, more preferably at least 90%, at least 95%, at least 97% or at least 99% or 100% sequence identity to the amino acid sequence as set forth in SEQ ID NO: 23, or the coding sequence thereof has at least 70%, preferably at least 80%, more preferably at least 90%, at least 95%, at least 97% or at least 99% or 100% sequence identity to the nucleic acid molecule as set forth in SEQ ID NO: 24. In an embodiment, the CD28 co-stimulatory domain has at least 70%, preferably at least 80%, more preferably at least 90%, at least 95%, at least 97% or at least 99% or 100% sequence identity to the amino acid sequence as set forth in SEQ ID NO: 21, or the coding sequence thereof has at least 70%, preferably at least 80%, more preferably at least 90%, at least 95%, at least 97% or at least 99% or 100% sequence identity to the nucleic acid molecule as set forth in SEQ ID NO: 22.

In an embodiment, the signaling domain consists of one or more co-stimulatory domains, that is, it does not comprise a primary signaling domain, such as a primary signaling domain from FcRγ, FcRβ, CD3γ, CD3δ, CD3ε, CD3ζ, CD22, CD79a, CD79b and CD66d. In another embodiment, the signaling domain of the chimeric receptor of the present disclosure may further comprise a primary signaling domain, such as the CD3ζ intracellular region. In a preferred embodiment, the CD3ζ intracellular region has at least 70%, preferably at least 80%, more preferably at least 90%, at least 95%, at least 97% or at least 99% or 100% sequence identity to the amino acid sequence as set forth in SEQ ID NO: 25 or 27, or the coding sequence thereof has at least 70%, preferably at least 80%, more preferably at least 90%, at least 95%, at least 97% or at least 99% or 100% sequence identity to the nucleic acid molecule as set forth in SEQ ID NO: 26 or 28.

In an embodiment, the chimeric receptor of the present disclosure may further comprise a hinge region located between the antibody and the transmembrane domain. As used herein, the term "hinge region" generally refers to any oligopeptide or polypeptide that functions to link a transmembrane domain to an antibody. Specifically, the hinge region serves to provide greater flexibility and accessibility to the antibody. The hinge region may comprise up to 300 amino acids, preferably 10 to 100 amino acids and most preferably 25 to 50 amino acids. The hinge region may be completely or partially derived from a natural molecule, for example, completely or partially from the extracellular region of CD8, CD4 or CD28, or completely or partially from an antibody constant region. Alternatively, the hinge region may be a synthetic sequence corresponding to a naturally occurring hinge sequence, or may be a completely synthetic hinge sequence. In a preferred embodiment, the hinge region comprises a hinge region portion of CD8α, CD28, an Fc γ RIII α receptor, IgG4, or IgG1, more preferably a hinge from CD8α, CD28 or IgG4, and has at least 70%, preferably at least 80%, more preferably at least 90%, at least 95%, at least 97% or at least 99% or 100% sequence identity to the amino acid sequence as set forth in SEQ ID NO: 33, 35 or 37, or the encoding sequence thereof has at least 70%, preferably at least 80%, more preferably at least 90%, at least 95%, at least 97% or at least 99% or 100% sequence identity to the nucleic acid molecule as set forth in SEQ ID NO: 34, 36 or 38.

In an embodiment, the CAR of the present disclosure may further comprise a signal peptide such that when it is expressed in a cell such as a T cell, the nascent protein is directed to the endoplasmic reticulum and subsequently to the cell surface. The core of the signal peptide may contain a long hydrophobic amino acid segment, which has a tendency to form a single α-helix. At the end of the signal peptide, there is usually an amino acid segment capable of being recognized and cleaved by signal peptidase. The signal peptidase may cleave during or after translocation, so as to generate free signal peptide and mature protein. Then, the free signal peptide is digested by a specific protease. Signal peptides that may be used in the present disclosure are well known to those skilled in the art, for example, signal peptides derived from B2M, CD8α, IgG1, GM-CSFRα, and the like. In an embodiment, the signal peptide that may be used in the present disclosure is from B2M or CD8α, and has at least 70%, preferably at least 80%, more preferably at least 90%, at least 95%, at least 97% or at least 99% or 100% sequence identity to an amino acid sequence as set forth in SEQ ID NO: 29 or 31, or the coding sequence thereof has at least 70%, preferably at least 80%, more preferably at least 90%, at least 95%, at least 97% or at least 99% or 100% sequence identity to the nucleic acid molecule as set forth in SEQ ID NO: 30 or 32.

In an embodiment, the CAR comprises the anti-NKG2A antibody as provided herein or the multispecific antibody comprising the anti-NKG2A antibody, a CD8α transmembrane region and a signaling domain, wherein the signaling domain comprises a co-stimulatory domain selected from the group consisting of CD28 and 4-1BB. Preferably, the signaling domain consists of a co-stimulatory domain selected from the group consisting of CD28 and 4-1BB. In another embodiment, the signaling domain further comprises a CD3ζ intracellular region. In this embodiment, the CAR may further comprise a signal peptide from B2M, CD8α, IgG1 or GM-CSFRα.

The present disclosure further provides a nucleic acid molecule encoding the NKG2A-targeting chimeric receptor as defined above, and a vector comprising the nucleic acid molecule.

As used herein, the term "vector" is an intermediary nucleic acid molecule used to transfer (exogenous) genetic material into a host cell, and in the host cell the nucleic acid molecule can be, for example, replicated and/or expressed. The vector generally includes targeting vectors and expression vectors. The "targeting vector" is a medium that delivers an isolated nucleic acid to the interior of a cell by, for example, homologous recombination or by using a hybridization recombinase specifically targeting a sequence at a site. The "expression vector" is a vector used for transcription of heterologous nucleic acid sequences (for example, those sequences encoding the chimeric receptor polypeptides of the present disclosure) in suitable host cells and the translation of their mRNAs. Suitable vectors that can be used in the present disclosure are known in the art, and many are commercially available. In an embodiment, the vector of the present disclosure includes, but is not limited to, plasmid, virus (e.g., retrovirus, lentivirus, adenovirus, vaccinia virus, Rous sarcoma virus (RSV), polyoma virus, and adeno-associated virus (AAV), etc.), phage, phagemid, cosmid, and artificial chromosome (including BAC and YAC). The vector itself is usually a nucleic acid molecule, and usually is a DNA sequence containing an insert (transgene) and a larger sequence as "backbone" of the vector. Engineered vector typically also contains an origin of autonomous replication in the host cell (if stable expression of polynucleotide is desired), a selectable marker, and a restriction enzyme cleavage site (e.g., a multiple cloning site, MCS). The vectors may additionally contain elements such as a promoter, a poly-A tail (polyA), 3' UTR, an enhancer, a terminator, an insulator, an operon, a selectable marker, a reporter gene, a targeting sequence, and/or a protein purification tag. In a specific embodiment, the vector is an in vitro transcription vector.

Engineered Immune Cells

NKG2A binds to non-classical HLA-class I molecules, such as HLA-E, thereby inhibiting the activation of immune cells such as NK cells. Therefore, The introduction of exogenous NKG2A antibodies can inhibit the killing effect of NK cells by binding to NKG2A, which is especially useful in some cases (such as in the absence of HLA-class I molecules or in the preparation of universal CAR-T cells).

Therefore, in an aspect, the present disclosure further provides an engineered immune cell, which expresses the chimeric receptor comprising the anti-NKG2A antibody of the present disclosure, wherein the expression of at least one MHC-related gene is suppressed or silenced. In a preferred embodiment, the engineered immune cell also expresses a second chimeric receptor comprising a second NK inhibitory ligand, wherein the second NK inhibitory ligand is an antibody or fragment thereof targeting other NK inhibitory receptors, and/or natural ligands of other NK inhibitory receptors or NK inhibitory receptor binding regions comprised therein.

As used herein, MHC-related genes include MHC genes themselves (e.g., MHC-class I molecules and MHC-class II molecules), as well as genes that interact with MHC genes or regulate the expression of MHC genes. Examples of MHC class I molecules include, but are not limited to, HLA-A, HLA-B, HLA-C, B2M. Examples of MHC class II molecules include, but are not limited to, HLA-DPA1, HLA-DQA1, and HLA-DRA. Examples of genes that interact with MHC genes or regulate the expression of MHC genes include, but are not limited to, TAP1, TAP2, LMP2, LMP7, RFX5, RFXAP, RFXANK, and CIITA.

Accordingly, in an embodiment, inhibiting or silencing the expression of MHC-related genes refers to inhibiting or silencing the expression of one or more genes selected from: HLA-A, HLA-B, HLA-C, B2M, HLA-DPA, HLA-DQ, HLA-DRA, TAP1, TAP2, LMP2, LMP7, RFX5, RFXAP, RFXANK, CIITA and a combination thereof, and preferably selected from the group consisting of HLA-A, HLA-B, HLA-C, B2M, RFX5, RFXAP, RFXANK, CIITA and a combination thereof.

In an embodiment, the engineered immune cell expressing the chimeric receptor comprising the anti-NKG2A antibody of the present disclosure further comprises suppressed or silenced expression of at least one TCR/CD3 gene, examples of which include TRAC, TRBC, CD3γ, CD3δ, CD3ε, CD3ζ.

In a preferred embodiment, the engineered immune cells expressing the chimeric receptor of the present disclosure include suppressed or silenced expression of at least one TCR/CD3 gene and at least one MHC-related gene, wherein the at least one TCR/CD3 gene is selected from the group consisting of TRAC, TRBC, CD3γ, CD3δ, CD3ε, CD3ζ and a combination thereof; the at least one MHC-related gene is selected from the group consisting of HLA-A, HLA-B, HLA-C, B2M, HLA-DPA, HLA-DQ, HLA-DRA, TAP1, TAP2, LMP2, LMP7, RFX5, RFXAP, RFXANK, CIITA and a combination thereof, and preferably selected from the group consisting of HLA-A, HLA-B, HLA-C, B2M, RFX5, RFXAP, RFXANK, CIITA and a combination thereof.

In a preferred embodiment, the at least one TCR/CD3 gene is selected from the group consisting of TRAC, TRBC and a combination thereof, and the at least one MHC-related gene is selected from the group consisting of B2M, RFX5, RFXAP, RFXANK, CIITA and a combination thereof. In an embodiment, the expression of TRAC or TRBC, and B2M of the engineered immune cells is inhibited or silenced. In an embodiment, the expression of TRAC or TRBC, and CIITA of the engineered immune cells is inhibited or silenced. In a preferred embodiment, the expression of TRAC or TRBC, B2M and CIITA of the engineered immune cells is suppressed or silenced. In a preferred embodiment, the expression of TRAC or TRBC, B2M and RFX5 of the engineered immune cells is inhibited or silenced.

Methods for inhibiting gene expression or gene silencing are well known to those skilled in the art, including but not limited to, for example, mediating DNA breakage by meganucleases, zinc finger nucleases, TALE nucleases, or Cas enzymes in the CRISPR system, or inactivating genes through technologies such as antisense oligonucleotides, RNAi, shRNA, etc.

In an embodiment, the engineered immune cell provided by the present disclosure further express a chimeric antigen receptor targeting a tumor antigen.

In an embodiment, the chimeric antigen receptor targets a tumor antigen selected from the group consisting of: TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD3δ, CD44v6, CEA, EPCAM, B7H3, KIT, IL-13Ra2, mesothelin, IL-11Ra, PSCA, PRSS21, VEGFR2, LewisY, CD24, PDGFR-β, SSEA-4, CD20, Folate receptor α, ERBB2 (Her2/ neu), MUC1, EGFR, NCAM, Prostase, PAP, ELF2M, Ephrin B2, IGF-I receptor, CAIX, LMP2, gplOO, bcr-abl, tyrosinase, EphA2, Fucosyl GM1, sLe, GM3, TGS5, HMWMAA, o-acetyl-GD2, Folate receptor β, TEM1/ CD248, TEM7R, CLDN6, GPRC5D, CXORF61, CD97, CD 179a, ALK, polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos associated antigen 1, p53, p53 mutant, prostate specific protein, survivin and telomerase, PCTA-1/ Galectin 8, MelanA/MART1, Ras mutant, hTERT, sarcoma translocation breakpoint, ML-IAP, ERG (TMPRSS2 ETS fusion gene), NA17, PAX3, androgen receptor, Cyclin B1, MYCN, RhoC, TRP-2, CYP1B 1, BORIS, SART3, PAX5, OY-TES 1, LCK, AKAP-4, SSX2, RAGE-1, human telomerase reverse transcriptase, RU1, RU2, intestinal tract carboxylesterase, mut hsp70-2, CD79a, CD79b, CD72, LAIR1, FCAR, LILRA2, CD300LF, CLEC12A, BST2, EMR2, LY75, GPC3, FCRL5, IGLL1, PD1, PDL1, PDL2, TGF β, APRIL, Claudin18.2, NKG2D and any combination thereof. Preferably, the target is selected from the group consisting of: CD19, CD20, CD22, BAFF-R, CD33, EGFRvIII, BCMA, GPRC5D, PSMA, ROR1, FAP, ERBB2 (Her2/ neu), MUC1, EGFR, CAIX, WT1, NY-ESO-1, CD79a, CD79b, GPC3, Claudin18.2, NKG2D, and any combination thereof. Depending on the antigen to be targeted, the chimeric antigen receptor of the disclosure may be designed to include an antibody specific for the antigen. For example, if CD19 is the antigen to be targeted, an anti-CD19 antibody may be used in the chimeric antigen receptor of the disclosure.

As used herein, the term "immune cell" refers to any cell of the immune system that has one or more effector functions (e.g., cytotoxic cell killing activity, secretion of cytokines, induction of ADCC and/or CDC). For example, the immune cell may be a T cell, a macrophage, a dendritic cell, a monocyte, an NK cell, and/or an NKT cell. In an embodiment, the immune cell is derived from a stem cell, such as an adult stem cell, an embryonic stem cell, a cord blood stem cell, a progenitor cell, a bone marrow stem cell, an induced pluripotent stem cell, a totipotent stem cell, or a hematopoietic stem cell, and so on. Preferably, the immune cell is a T cell. The T cell may be any T cell, such as in vitro cultured T cell, for example, primary T cell, or T cell from in vitro cultured T cell line, e.g., Jurkat, SupT1, etc., or T cell obtained from a subject. Examples of subject include humans, dogs, cats, mice, rats, and transgenic species thereof. The T cell may be obtained from a variety of sources, including peripheral blood monocytes, bone marrow, lymph node tissue, umbilical blood, thymus tissue, tissue from sites of infection, ascites, pleural effusion, spleen tissue, and tumors. The T cell also may be concentrated or purified. The T cell may be at any stage of development including, but not limited to, a CD4+/ CD8+ T cell, a CD4+ helper T cell (e.g., Th1 and Th2 cells), CD8+ T cell (e.g., cytotoxic T cell), tumor infiltrating cell, memory T cell, naive T cell, γδ-T cell, αβ-T cell. In a preferred embodiment, the immune cell is a human T cell. The T cell may be isolated from the blood of a subject using a variety of techniques known to those of skill in the art, such as Ficoll.

The nucleic acid sequence encoding the chimeric receptor may be introduced into an immune cell using conventional methods known in the art (e.g., by transduction, transfection, transformation). "Transfection" is a process of introducing a nucleic acid molecule or polynucleotide (including a vector) into a target cell. An example is RNA transfection, i.e., the process of introducing RNA (e.g., in vitro transcribed RNA, ivtRNA) into a host cell. This term is mainly used for a non-viral method in eukaryotic cells. The term "transduction" is generally used to describe virus-mediated transfer of nucleic acid molecules or polynucleotides. Transfection of animal cells typically involves opening transient pores or "holes" in the cell membrane, so as to allow uptake of material. Transfection may be carried out using calcium phosphate, by electroporation, by extrusion of cells, or by mixing cationic lipids with the material so as to produce liposomes which fuse with the cell membrane and deposit their cargo into the interior. Exemplary techniques for transfecting eukaryotic host cells include lipid vesicle-mediated uptake, heat shock-mediated uptake, calcium phosphate-mediated transfection (calcium phosphate/DNA co-precipitation), microinjection, and electroporation. The term "transformation" is used to describe the non-virus transfer of a nucleic acid molecule or polynucleotide (including a vector) to bacteria, and also to non-animal eukaryotic cells (including plant cells). Thus, the transformation is a genetic alteration of bacterial or non-animal eukaryotic cells, which is produced by direct uptake of a cell membrane from its surroundings and subsequent incorporation of exogenous genetic material (nucleic acid molecule). The transformation may be achieved by artificial means. In order for transformation to occur, the cell or bacterium must be in a competent state. For prokaryotic transformation, the techniques may include heat shock-mediated uptake, fusion to bacterial protoplasts of intact cells, microinjection, and electroporation. After the nucleic acid or vector is introduced into the immune cells, those skilled in the art may amplify and activate the obtained immune cells by conventional techniques.

In an embodiment, the present disclosure further provides a plurality of engineered immune cells, wherein an immune cell expresses the chimeric receptor of the present disclosure and optionally a chimeric antigen receptor targeting a tumor antigen, and another immune cell expresses a second chimeric receptor targeting other NK inhibitory receptors. In this embodiment, the second chimeric receptor comprises a second NK inhibitory ligand, a transmembrane domain and a signaling domain, wherein the second NK inhibitory ligand, transmembrane domain and signaling domain are defined as described in the "Chimeric Receptors" section. In such embodiments, the plurality of engineered immune cells may be administered together or separately. In an embodiment, the plurality of immune cells may be in the same composition or in different compositions. Exemplary compositions of cells include those described in the following sections of this application.

Antibody Conjugate

In an aspect, the present disclosure provides an antibody conjugate comprising the anti-NKG2A antibody as defined herein and a second functional structure, wherein the second functional structure is selected from the group consisting of an Fc, a radioisotope, a structure moiety for extending half-life, a detectable marker and a drug.

In an embodiment, the present disclosure provides an antibody conjugate comprising the anti-NKG2A antibody as defined in the present disclosure and Fc. As used herein, the term "Fc" is used to define the C-terminal region of an immunoglobulin heavy chain, and includes natural Fc and variant Fc. "Natural Fc" refers to a molecule or sequence comprising a non-antigen-binding fragment, whether monomeric or multimeric, produced by digestion of an intact antibody. The source of immunoglobulin from which natural Fc is produced is preferably of human origin. Natural Fc fragments are composed of monomeric polypeptides that can be linked as dimers or multimers through covalent linkages (e.g., disulfide bonds) and non-covalent linkages. Depending on the class (e.g., IgG, IgA, IgE, IgD, IgM) or subtype (e.g., IgG1, IgG2, IgG3, IgA1, IgGA2), natural Fc molecules have 1-4 intermolecular disulfide bonds between monomeric subunits. An example of a natural Fc is a disulfide-linked dimer produced by papain digestion of IgG (see Ellison et al. (1982), Nucleic Acids Res. 10:4071-9). The term "natural Fc" as used herein generally refers to monomeric, dimeric and multimeric forms. A "variant Fc" refers to an amino acid sequence that differs from that of a "natural" or "wild-type" Fc by virtue of at least one "amino acid modification" as defined herein, also referred to as an "Fc variant". Thus, "Fc" also includes single-chain Fc (scFc), i.e., a single-chain Fc consisting of two Fc monomers linked by a polypeptide linker, which is capable of naturally folding into a functional dimeric Fc region. In an embodiment, the Fc is preferably the Fc of a human immunoglobulin, more preferably the Fc of a human IgG1.

In an embodiment, the present disclosure provides an antibody conjugate comprising the anti-NKG2A antibody as defined in the present disclosure and a radioactive isotope. Examples of radioisotopes useful in the present disclosure include, but are not limited to, At211, I131, I125, Y90, Re186, Re188, Sm153, Bi212, P32, Pb212, 99mTc, 123I, 18F, and 68Ga.

In an embodiment, the present disclosure provides an antibody conjugate comprising the anti-NKG2A antibody as defined in the present disclosure and a structure moiety for extending half-life selected from the group consisting of an albumin-binding structure, a transferrin-binding structure, a polyethylene glycol molecule, a recombinant polyethylene glycol molecule, a human serum albumin, a fragment of human serum albumin, and a polypeptide binding to human serum albumin (including antibody).

In an embodiment, the present disclosure provides an antibody conjugate comprising the anti-NKG2A antibody as defined in the present disclosure and a detectable marker. The term "detectable marker" means herein a compound that produces a detectable signal. For example, the detectable marker may be an MRI contrast agent, a scintigraphy contrast agent, an X-ray imaging contrast agent, an ultrasound contrast agent, an optical imaging contrast agent. Examples of detectable markers include fluorophores (e.g., fluorescein, Alexa, or cyanine), chemiluminescent compounds (e.g., luminol), bioluminescent compounds (e.g., luciferase or alkaline phosphatase), enzymes (e.g., horseradish peroxidase, glucose-6-phosphatase, β-galactosidase), antibiotics (e.g., kanamycin, ampicillin, chloramphenicol, tetracycline, etc.) resistance genes, and contrast agents (e.g., nanoparticles or gadolinium). Those skilled in the art can select an appropriate detectable marker according to the detection system used.

In an embodiment, the present disclosure provides an antibody conjugate comprising the anti-NKG2A antibody as defined in the present disclosure and a drug conjugated to the anti-NKG2A antibody, such as a cytotoxin or an immunomodulator (i.e., an antibody-drug conjugate). Usually, the drug is covalently linked to the antibody, usually by a linker. In an embodiment, the drug is a cytotoxin. In another embodiment, the drug is an immunomodulator. Examples of cytotoxins include, but are not limited to, methotrexate, aminopterin, 6-mercaptopurine, 6-thioguanine, cytarabine, 5-fluorouracil, dacarbazine, nitrogen mustard, thiotepa, chlorambucil, melphalan, carmustine (BSNU), lomustine (CCNU), 1-methylnitrosourea, cyclophosphamide, nitrogen mustard, busulfan, dibromomannitol, streptozocin, mitomycin, cis-dichlorodiamine platinum (II) (DDP), cisplatin, carboplatin, zorubicin, doxorubicin, detorubicin, carminomicin, idarubicin, epirubicin, mitoxantrone, actinomycin D, bleomycin, calicheamicin, mithramycin, anthramycin (AMC), vincristine, vinblastine, paclitaxel, ricin, pseudomonas exotoxin, gemcitabine, cytochalasin B, gramicidin D, ethidium bromide, emetine, etoposide, teniposide, colchicine, mitoxantrone, 1-dehydrotestosterone, glucocorticoid, procaine, tetracaine, lidocaine, propranolol, puromycin, procarbazine, hydroxyurea, asparaginase, corticosteroids, mitotane (O,P'-(DDD)), interferon, and a combination thereof. Examples of immunomodulators include, but are not limited to, ganciclovir, etanercept, tacrolimus, sirolimus, voclosporin, cyclosporine, rapamycin, cyclophosphamide, azathioprine, mycophenolate mofetil, methotrexate, glucocorticoid and analogs thereof, cytokines, stem cell growth factors, lymphotoxins, tumor necrosis factor (TNF), hematopoietic factors, interleukins (e.g., IL-1, IL-2, IL-3, IL-6, IL-10, IL-12, IL-18 and IL-21), colony-stimulating factors (e.g., G-CSF and GM-CSF), interferons (e.g., interferon-α, interferon-beta and interferon-gamma), stem cell growth factor designated "S1 factor", erythropoietin and thrombopoietin, or a combination thereof.

Kits and Pharmaceutical Compositions

In another aspect, the present disclosure further provides a detection kit comprising the antibody, the multispecific antibody, the chimeric receptor or the antibody conjugate of the present disclosure.

In another aspect, the present disclosure further provides a pharmaceutical composition comprising the antibody, the chimeric receptor, the multispecific antibody, or the antibody conjugate described in the present disclosure, and one or more pharmaceutically acceptable excipients.

As used herein, the term "pharmaceutically acceptable excipient" refers to a carrier and/or excipient that is pharmacologically and/or physiologically compatible (i.e., capable of triggering a desired therapeutic effect without causing any undesired local or systemic effects) with the subject and active ingredient, and it is well known in the art (see, e.g., Remington's Pharmaceutical Sciences. Edited by Gennaro A R, 19th ed. Pennsylvania: Mack Publishing Company, 1995). Examples of pharmaceutically acceptable excipient include, but are not limited to, filler, binder, disintegrant, coating agent, adsorbent, anti-adherent, glidant, antioxidant, flavoring agent, colorant, sweetener, solvent, co-solvent, buffer agent, chelating agent, surfactant, diluent, wetting agent, preservative, emulsifier, cladding agent, isotonic agent, absorption delaying agent, stabilizer, and tension regulator. It is known to those skilled in the art to select a suitable excipient to prepare the desired pharmaceutical composition of the present disclosure. Exemplary excipients for use in the pharmaceutical composition of the present disclosure include saline, buffered saline, dextrose, and water. Generally, the selection of a suitable excipient depends, in particular, on the active agent used, the disease to be treated, and the desired dosage form of the pharmaceutical composition.

The pharmaceutical composition according to the present disclosure is suitable for multiple routes of administration. Generally, the administration is parenterally accomplished. Parenteral delivery methods comprise topical, intraarterial, intramuscular, subcutaneous, intramedullary, intrathecal, intraventricular, intravenous, intraperitoneal, intrauterine, intravaginal, sublingual, or intranasal administration.

The pharmaceutical composition according to the present disclosure also may be prepared in various forms, such as solid, liquid, gaseous or lyophilized forms, particularly the pharmaceutical composition can be prepared in the form of ointment, cream, transdermal patch, gel, powder, tablet, solution, aerosol, granule, pill, suspension, emulsion, capsule, syrup, elixir, extract, tincture or liquid extract, or in a form particularly suitable for the desired method of administration. Processes known in the present disclosure for producing a medicine may include, for example, conventional mixing, dissolving, granulating, dragee-making, grinding, emulsifying, encapsulating, embedding or lyophilizing process. The pharmaceutical composition containing, for example, the immune cell as described herein is generally provided in a form of solution, and preferably contains a pharmaceutically acceptable buffer agent.

The pharmaceutical composition according to the present disclosure further may be administered in combination with one or more other agents suitable for the treatment and/or prophylaxis of diseases to be treated. Preferred examples of agent suitable for the combination include known anti-cancer medicines such as cisplatin, maytansine derivatives, rachelmycin, calicheamicin, docetaxel, etoposide, gemcitabine, ifosfamide, irinotecan, melphalan, mitoxantrone, sorfimer sodiumphotofrin II, temozolomide, topotecan, trimetreate glucuronate, auristatin E, vincristine and doxorubicin; peptide cytotoxins, such as ricin, diphtheria toxin, pseudomonas exotoxin A, DNase and RNase; radionuclides such as iodine 131, rhenium 186, indium 111, iridium 90, bismuth 210, bismuth 213, actinides 225 and astatine 213; prodrugs such as antibody-directed enzyme prodrugs; immunostimulatory agents such as platelet factor 4, and melanoma growth stimulating protein; antibodies or fragments thereof, such as anti-CD3 antibodies or fragments thereof, complement activators, heterologous protein domains, homologous protein domains, viral/bacterial protein domains and viral/bacterial peptides. In addition, the pharmaceutical composition of the present disclosure also can be used in combination with one or more other treatment methods, such as chemotherapy and radiotherapy.

Therapeutic/Preventive/Diagnostic Use

In another aspect, the present disclosure further provides a method for treating and/or preventing and/or diagnosing diseases associated with NKG2A expression, comprising administering to a subject the antibody, the multispecific antibody, the antibody conjugate or the pharmaceutical composition as described above.

In an embodiment, diseases associated with NKG2A expression include cancer, infectious diseases, inflammatory diseases and autoimmune diseases. Examples of cancers that can be treated with the antibodies of the invention include, but are not limited to: solid cancers, including bladder cancer, breast cancer, colon cancer, kidney cancer, liver cancer, lung cancer, ovarian cancer, prostate cancer, pancreatic cancer, gastric cancer, cervical cancer, thyroid cancer and skin cancer, including squamous cell carcinoma; lymphoid hematopoietic neoplasms, including leukemia, acute lymphocytic leukemia, chronic lymphocytic leukemia, acute lymphoblastic leukemia, B-cell lymphoma, T-cell lymphoma, Hodgkin's lymphoma, non-Hodgkin lymphoma, hairy cell lymphoma, and Burkitt lymphoma, and multiple myeloma; myeloid hematopoietic neoplasms, including acute and chronic myeloid leukemia, promyelocytic leukemia, and myelodysplastic syndrome; tumors of mesenchymal origin, including fibrosarcoma and rhabdomyosarcoma; other tumors, including melanoma, seminoma, teratocarcinoma, neuroblastoma, and glioma; central and peripheral nervous system tumors, including astrocytoma, neuroblastoma, glioma, and schwannoma; tumors of mesenchymal origin, including fibrosarcoma, rhabdomyosarcoma, and osteosarcoma; and other neoplasms, including melanoma, xeroderma pigmentosa, keratoacanthoma, seminoma, follicular carcinoma of the thyroid, and teratocarcinoma. Examples of infectious diseases that can be treated with the antibodies of the invention include, but are not limited to, infections caused by viruses, bacteria, protozoa, or fungi, where viruses include, for example, hepatitis A virus, hepatitis B virus, hepatitis C virus, influenza virus, varicella virus, adenovirus, herpes simplex type 1 (HSV-1), herpes simplex type 2 (HSV-2), rinderpest, rhinovirus, echovirus, rotavirus, respiratory syncytial virus, papilloma virus, cytomegalovirus, arbovirus, coxsackie virus, mumps virus, measles virus, rubella virus, polio virus, human immunodeficiency virus type 1 or 2 (HIV-1, HIV-2); bacteria include, for example, *Staphylococcus, Streptococcus, Bacillus, Lactobacillus, Listeria, Corynebacterium diphtheriae* and the like. Examples of inflammatory diseases that can be treated with the antibodies of the invention include, but are not limited to: adrenalitis, alveolitis, angiocholecystitis, appendicitis, balanitis, blepharitis, bronchitis, bursitis, carditis, cellulitis, cervicitis, cholecystitis, chorditis vocalis, cochleitis, colitis, conjunctivitis, cystitis, dermatitis, diverticulitis, encephalitis, endocarditis, esophagitis, eustachitis, fibrositis, folliculitis, gastritis, gastroenteritis, gingivitis, glossitis, hepatosplenitis, keratitis, otitis interna, laryngitis, lymphangitis, mastitis, otitis media, meningitis, metritis, mucositis, etc. Examples of autoimmune diseases that can be treated with the antibodies of the invention include, but are not limited to: hemolytic anemia, pernicious anemia, polyarteritis nodosa, systemic lupus erythematosus, Wegener's granulomatous disease, autoimmune hepatitis, Behcet's disease, Crohn's disease, primary biliary cirrhosis, scleroderma, ulcerative colitis, sjogren's syndrome, type 1 diabetes, uveitis, Graves'disease, Alzheimer's disease, psoriasis, vitiligo, etc.

In another embodiment, when the chimeric receptor comprising the anti-NKG2A antibody of the present disclosure is co expressed with a chimeric antigen receptor targeting a tumor antigen in immune cells, the disease that can be treated depends on the tumor antigens targeted by the chimeric antigen receptors. For example, when the chimeric receptor comprising an anti-NKG2A antibody of the present disclosure is coexpressed or co-administered with a CD19-targeting chimeric antigen receptor, the disease that can be treated is a disease associated with CD19 expression, such as a B-cell malignancy, including acute lymphocytic leukemia (B-ALL), chronic B-lymphocytic leukemia (B-CLL), Bcell Hodgkin's lymphoma (B-HL) and non-Hodgkin's lymphoma (B-NHL), etc. In this embodiment, the chimeric receptor comprising an anti-NKG2A antibody is used to inhibit the killing of reinfused engineered immune cells by NK cells, and the chimeric antigen receptor is used to direct the killing to target cells by binding to tumor antigens.

The present disclosure will be described in detail below with reference to the accompanying drawings and examples. It should be noted that those skilled in the art should understand that the drawings and the embodiments of the present disclosure are only for the purpose of illustration, and shall not constitute any limitation to the present disclosure. In the case of no contradiction, the embodiments in the present application and the features in the embodiments can be combined with each other.

EXAMPLES

Example 1. Preparation of NKG2A Antibodies

In order to enhance the affinity and specificity of the antibody, a new anti-NKG2A antibody was prepared based on the humanized Z199 antibody (hZ199) by back mutation. hZ199 comprises CDR-L1 as set forth in SEQ ID NO: 1, CDR-L2 as set forth in SEQ ID NO: 2, CDR-L3 as set forth in SEQ ID NO: 3, CDR-H1 as set forth in SEQ ID NO: 4, CDR-H2 as set forth in SEQ ID NO: 5, and CDR-H3 as set forth in SEQ ID NO: 6. The amino acid sequence of the light chain variable region set forth in SEQ ID NO: 7, the amino acid sequence of the heavy chain variable region set forth in SEQ ID NO: 8, and the full-length amino acid sequence set forth in SEQ ID NO: 9. Methods of back mutation are known in the art, for example. designing back mutation primers according to some amino acids (mainly the framework region) in the hZ199 sequence that may affect the affinity of the antibody, designing 5 mutation points in the light chain variable region, and 4 mutation points in the heavy chain variable region, and finally two back mutant antibodies were obtained by combination, named hZ199-V1 and hZ199-V2, whose sequences are shown in Table 1 and FIG. 1.

TABLE 1

Sequences of hZ199 and its back mutant antibodies

| | hZ199 | hZ199-V1 | hZ199-V2 |
|---|---|---|---|
| VL | SEQ ID NO: 7 | SEQ ID NO: 10 | SEQ ID NO: 13 |
| VH | SEQ ID NO: 8 | SEQ ID NO: 11 | SEQ ID NO: 11 |
| full length | SEQ ID NO: 9 | SEQ ID NO: 12 | SEQ ID NO: 14 |

Example 2. Preparation of UNKi-T Cells Expressing Chimeric Receptors Containing Anti-NKG2A Antibodies and Verification of their Functions Sequences encoding the following proteins were synthesized and cloned into the pLVX vector (Public Protein/Plasmid Library (PPL), Cat. No.: PPL00157-4a): B2M signal peptide (SEQ ID NO: 29), hZ199 (SEQ ID NO: 9) or hZ199-V1 (SEQ ID NO: 12), CD28 hinge region (SEQ ID NO: 35), CD8α transmembrane region (SEQ ID NO: 17), CD28 costimulatory domain (SEQ ID NO: 21), to obtain hZ199 plasmid and hZ199-V1 plasmid, and the correct insertion of the target sequence in the plasmid was confirmed by sequencing.

Sequences encoding the following proteins were synthesized and cloned into the pLVX vector (Public Protein/Plasmid Library (PPL), Cat. No.: PPL00157-4a): CD8α signal peptide (SEQ ID NO: 31), hZ199-V2 (SEQ ID NO: 14), IgG4 hinge region (SEQ ID NO: 37), CD28 transmembrane region (SEQ ID NO: 19), 4-1BB co-stimulatory domain (SEQ ID NO: 23), to obtain hZ199-V2 plasmid, and the correct insertion of the target sequence in the plasmid was confirmed by sequencing.

Three ml Opti-MEM (Gibco, Cat. No. 31985-070) was added to a sterile tube to dilute the above plasmid, and then packaging vector psPAX2 (Addgene, Cat. No. 12260) and envelope vector pMD2. G (Addgene, Cat. No. 12259) were added according to the ratio of plasmid:viral packaging vector:viral envelope vector=4:2:1. Then, 120 μl X-treme GENE HP DNA transfection reagent (Roche, Cat. No. 06366236001) was added, mixed immediately, and incubated at room temperature for 15 min, and then the plasmid/vector/transfection reagent mixture was added dropwise to the culture flask containing 293T cells. Viruses were collected at 24 hours and 48 hours, pooled, and ultracentrifuged (25000 g, 4° C., 2.5 hours) to obtain concentrated lentivirus.

T cells were activated with DynaBeads CD3/ CD28 CTSTM (Gibco, Cat. No. 40203D), and were further cultured for 1 day at 37° C. and 5% CO2. Then, the concentrated lentivirus was added, and after 3 days of continuous culture, T cells expressing the chimeric receptor containing NKG2A antibody were obtained.

Then the CRISPR/Cas9 system was used to knock out TCR/CD3 components (specifically the TRAC gene) and MHC-related genes (specifically B2M and RFX5) in wild-type T cells (i.e. NT cells) and T cells expressing chimeric receptors containing anti-NKG2A antibodies, to obtain Mock T cells, UNKi-hZ99-T cells (containing hZ199 plasmid), UNKi-V1-T cells (containing hZ199-V1 plasmid) and UNKi-V2-T cells (containing hZ199-V2 plasmid), respectively. Using FITC Mouse Anti-Human CD3 (BD Pharmingen, Cat. No. 555916) antibody, PE mouse anti-human HLA-I (R&D Cat. No. FAB7098P) and APC anti-human DR, DP, DQ (biolegend, Cat. No. 361714) antibody, the expression efficiency of CD3/ HLA-I/HLA-II in the UNKi-T cells, Mock T cells and NT cells was detected by flow cytometry, and the results are shown in Table 2 below.

TABLE 2

| Gene expression efficiency in UNKi-T cells | | | |
|---|---|---|---|
| Cell name | TCR/CD3 | B2M/HLA-I | RFX5/HLA-II |
| UNKi-hZ199-T | 2.1% | 13% | 12.8% |
| UNKi-V1-T | 4.5% | 17.9% | 11.3% |
| UNKi-V2-T | 3.9% | 16.8% | 11.5% |
| Mock T | 3.7% | 14.8% | 11.8% |
| NT | 98% | 98% | 87% |

It can be seen from Table 2 that the expression of CD3/ HLA-I/HLA-II in UNKi-T cells and Mock T cells prepared in the present disclosure is effectively suppressed or silenced.

Figure 2:
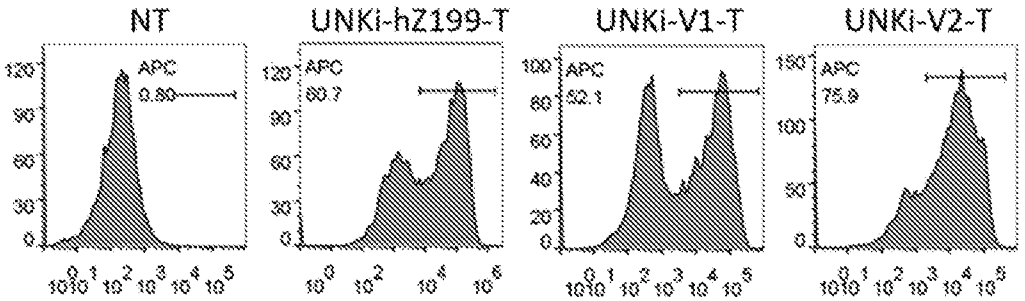
FIG. 2 shows scFv expression levels of UNKi-T cells containing NKG2A antibodies.

The expression level of anti-NKG2A scFv in the UNKi-T cells and Mock T cells was detected using Biotin-SP (long spacer) AffiniPure Goat Anti-Human IgG, F(ab') fragment specific antibody (Jackson ImmunoResearch, Cat. No. 109-065-097) and APC Streptavidin (BD, Cat. No. 554067) (FIG. 2).

It can be seen that all the scFvs in the UNKi-T cells prepared in the present disclosure are effectively expressed.

The inhibitory effect of the UNKi-T cells prepared by the present disclosure on the killing effect of NK cells was detected according to the following method: the UNKi-T cells and Mock-T cells prepared in the present disclosure were labeled with Far-Red (invitrogen, product number C34564). Then, the labeled UNKi-T cells and Mock T cells were plated into 96-well plates at a concentration of $1\times10^4$ cells/well, and NK92 cells were added at an effector-to-target ratio of 2:1 for co-culture. After 16-18 hours, the proportion of T cells in the culture was detected by flow cytometry, and then the killing rate of NK cells on T cells was calculated. The results are shown in FIG. 3.

Figure 3:
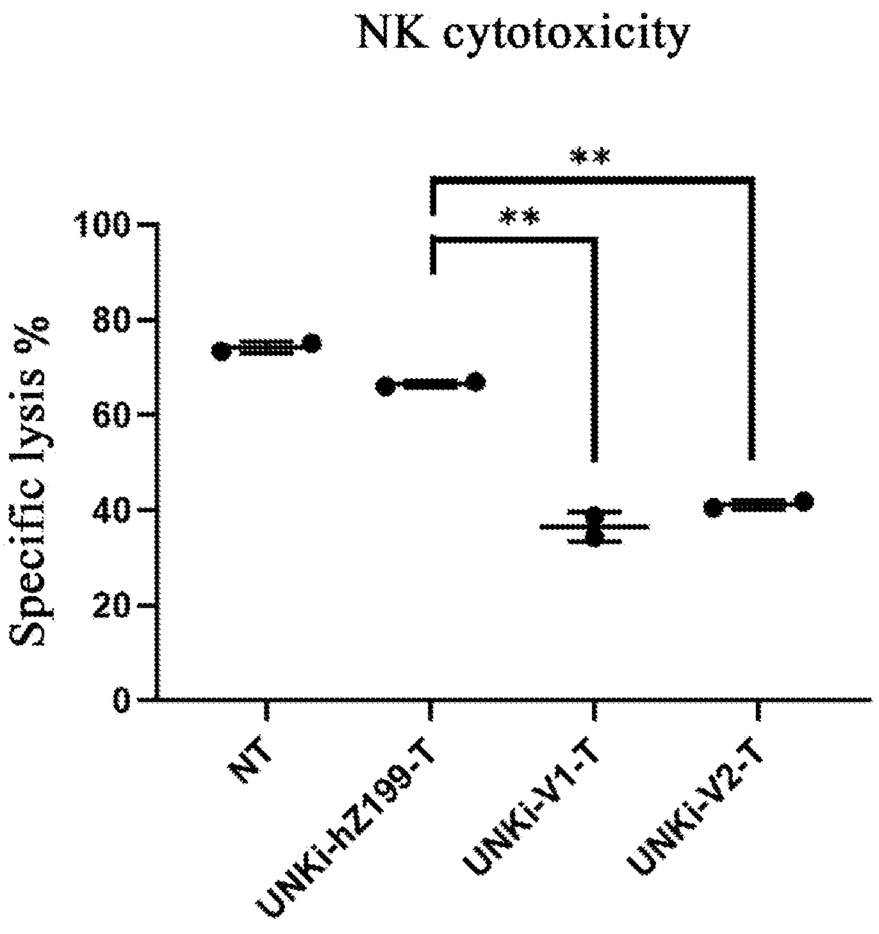
FIG. 3 shows the inhibitory effect of UNKi-T cells containing NKG2A antibodies on NK cell killing. Two-way ANOVA was used for analysis, and T test was used for statistical analysis. ** indicates that the P value is less than 0.01, reaching a significant level.

It can be seen from FIG. 3 that, compared with NT cells not expressing chimeric receptors, the UNKi-T cells of the present disclosure significantly reduce the killing effect of NK cells on T cells. In addition, compared with the hZ199 antibody, the antibodies of the present disclosure (i.e., back mutant antibodies hZ199-V1 and hZ199-V2) have a better inhibitory effect on NK cell killing, indicating that the affinity of the antibodies of the present disclosure is greater than that of the hZ199 antibody.

It should be noted that the above-mentioned are merely for preferred examples of the present disclosure and not used to limit the present disclosure. For one skilled in the art, various modifications and changes may be made to the present disclosure. Those skilled in the art should understand that any amendments, equivalent replacements, improvements, and so on, made within the spirit and principle of the present disclosure, should be covered within the scope of protection of the present disclosure.

What is claimed is:

1. A NKG2A-targeting antibody, comprising a light chain variable region and a heavy chain variable region, wherein the light chain variable region has an amino acid sequence selected from the group consisting of SEQ ID NOs: 10 or 13, the heavy chain variable region has an amino acid sequence as set forth in SEQ ID NO: 11.

2. A multispecific antibody comprising the antibody according to claim 1 and one or more second antibodies or antigen-binding portions thereof that specifically bind to antigens different from NKG2A.

3. An antibody conjugate comprising the antibody according to claim 1, and a second functional structure, wherein the second functional structure is selected from the group consisting of an Fc, a radioisotope, a structure moiety for extending half-life, a detectable marker and a drug.

4. A detection kit comprising the antibody according to claim 1.

5. A pharmaceutical composition comprising the antibody according to claim 1, and one or more pharmaceutically acceptable excipients.

* * * * *